United States Patent
Brannon

(10) Patent No.: US 7,445,595 B2
(45) Date of Patent: Nov. 4, 2008

(54) ENDOSCOPIC BONE DEBRIDEMENT

(75) Inventor: James Kevin Brannon, 5729 Canterbury Dr., Culver City, CA (US) 90230

(73) Assignee: James Kevin Brannon, Leawood, KS (US)

(*) Notice: Subject to any disclaimer, the term of this patent is extended or adjusted under 35 U.S.C. 154(b) by 433 days.

(21) Appl. No.: 10/928,553

(22) Filed: Aug. 26, 2004

(65) Prior Publication Data

US 2005/0234464 A1 Oct. 20, 2005

Related U.S. Application Data

(62) Division of application No. 09/957,817, filed on Sep. 19, 2001, now abandoned.

(51) Int. Cl.
*A61B 1/00* (2006.01)
*A61B 17/56* (2006.01)

(52) U.S. Cl. .......................... 600/114; 606/89
(58) Field of Classification Search ............... 600/102, 600/114, 105; 606/86, 89, 95, 96
See application file for complete search history.

(56) References Cited

U.S. PATENT DOCUMENTS

| | | | | |
|---|---|---|---|---|
| 3,822,697 A | * | 7/1974 | Komiya | 600/114 |
| 4,449,532 A | * | 5/1984 | Storz | 606/191 |
| 4,696,308 A | * | 9/1987 | Meller et al. | 600/567 |
| 4,765,314 A | * | 8/1988 | Kolditz et al. | 600/114 |
| 5,287,845 A | | 2/1994 | Faul et al. | 600/135 |
| 5,400,767 A | | 3/1995 | Murdoch | 600/157 |
| 5,413,578 A | * | 5/1995 | Zahedi | 606/86 |
| 5,441,503 A | | 8/1995 | Considine et al. | 606/115 |
| 5,464,008 A | | 11/1995 | Kim | 600/157 |
| 5,575,756 A | | 11/1996 | Karasawa et al. | 600/157 |
| 5,681,262 A | | 10/1997 | Isse | 600/127 |
| 5,827,312 A | | 10/1998 | Brown et al. | 606/167 |
| 5,899,908 A | * | 5/1999 | Kuslich et al. | 606/96 |
| 6,086,530 A | | 7/2000 | Mack | 600/121 |
| 6,142,931 A | * | 11/2000 | Kaji | 600/114 |

(Continued)

OTHER PUBLICATIONS

Brown, Thomas, et al., Mechanical Consequences of Core Drilling and Bone-Grafting on osteonecrosis of the Femoral Head, The Journal of Bone and Joint Surgery, Incorporated vol. 75-A, No. 9, Sep. 1993, 1358-13367.

(Continued)

*Primary Examiner*—John P Leubecker
(74) *Attorney, Agent, or Firm*—Intellectual Property Center LLC; Arthur K. Shaffer

(57) ABSTRACT

The invention described includes an osteoendoscopic cylinder for tamponading bleeding along a longitudinal canal surface of an osteocentral canal of a femoral neck so as to allow endoscopic visualization of a segment of osteonecrotic bone within a femoral head. The osteoendoscopic cylinder is of a dimension adapted to receive an endoscope therein and includes an inner visual surface and an outer bony contact surface. An orientation mark along the inner visual surface is of a size and dimension to ensure a first visualization thereof with the endoscope. The first visualization is of an effect to allow spatial orientation of the endoscope within the femoral head. A side opening proximally situated thereabout a proximal handle end is of a size and dimension adapted to mount a vacuum apparatus comprising of a transparent tube.

6 Claims, 15 Drawing Sheets

U.S. PATENT DOCUMENTS

| | | | |
|---|---|---|---|
| 6,248,110 B1 * | 6/2001 | Reiley et al. | 606/93 |
| 6,315,714 B1 | 11/2001 | Akiba | 600/114 |
| 6,354,992 B1 | 3/2002 | Kato | 600/157 |
| 6,440,061 B1 * | 8/2002 | Wenner et al. | 600/114 |
| 6,520,907 B1 * | 2/2003 | Foley et al. | 600/114 |

OTHER PUBLICATIONS

Marcus, Neal, Enneking, W.F., The Silent Hip in Idiopathic Aseptic Necrosis, Treatment by Bone Grating, JBJS vol. 55A, No. 7, Oct. 1973, 1351-1366.

Trabecular Metal, The Best Thing Next to Bone, Zimmer Brochure, 2000.

Urbaniak, James R. , Harvey, Edward, Revascularization of the Femoral Head in Osteonecrosis, Journal of the American Academy of Orthopaedic Surgeons, 1998; 6:44-54.

Moore, Richard S., The Role of Free Vascularized Grafts in the Management of Osteonecrosis of the Femorral Head, The University of Penn. Ortho. Journal, 13: 89-95, 2000.

Garino, Jonathan P., The Treatment of Avascular Necrosis of the Femoral Head—A Commentary, The University of Penn. Ortho. Journal, 13: 96, 2000.

Steinberg, Marvin, The Advantages of Core Decompression for Treating Avascular Necrosis, The University of Penn. Ortho. Journal, 13: 84-88, 2000.

Enneking, William F., Campanacci, Domenico A., Retrieved Human Allografts, The Journal of Bone and Joint Surgery (American) 83:971-986 (2001).

Lavernia, Carlos J., Sierra, Rafael J., Grieco, Francisco R., Osteonecrosis of the Femoral Head, Journal of the American Academy of Orthopaedic Surgeons, 1999, 7:250-261.

* cited by examiner $$I = \tfrac{1}{4}\pi(R^4 - r^4)$$

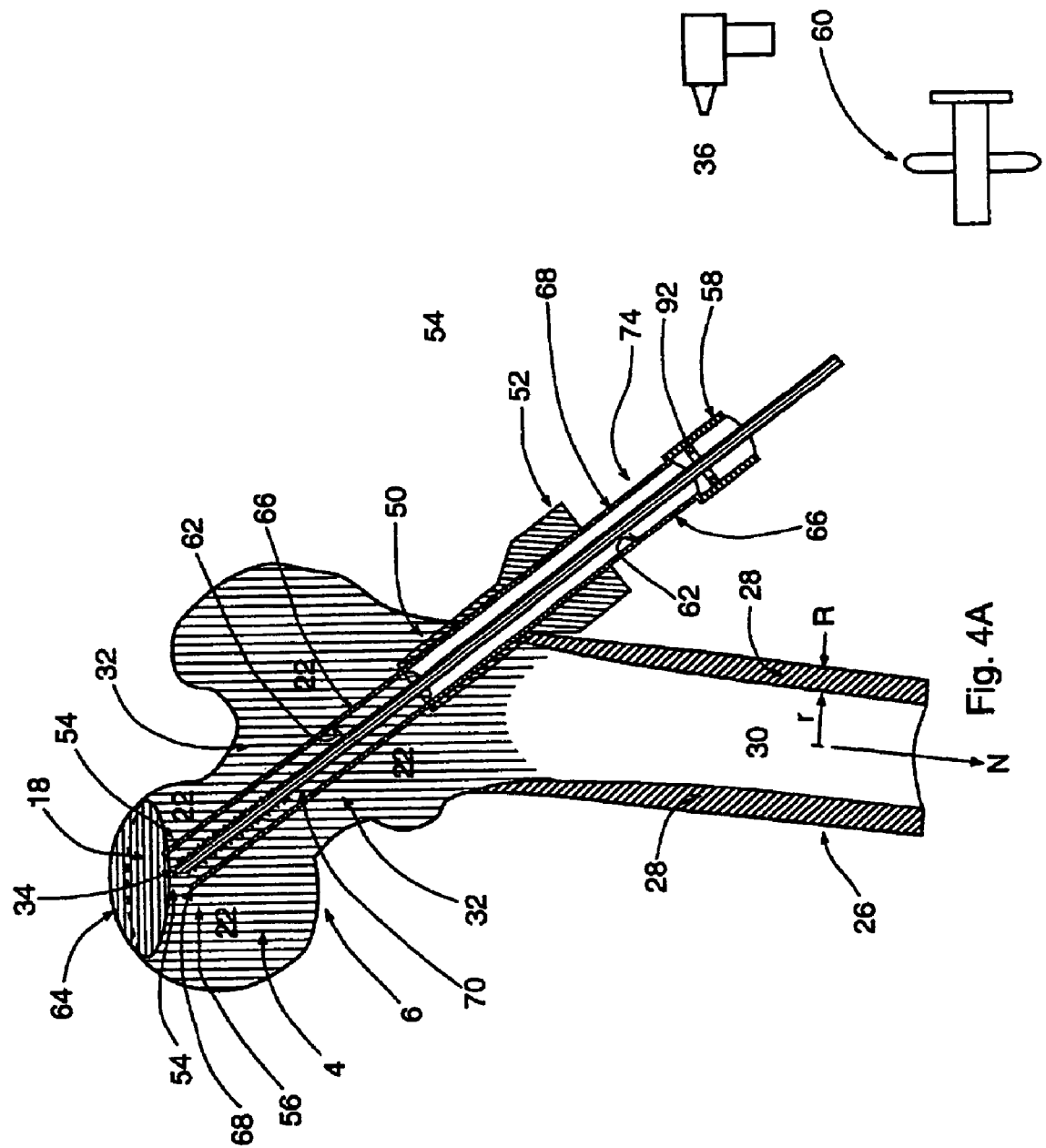

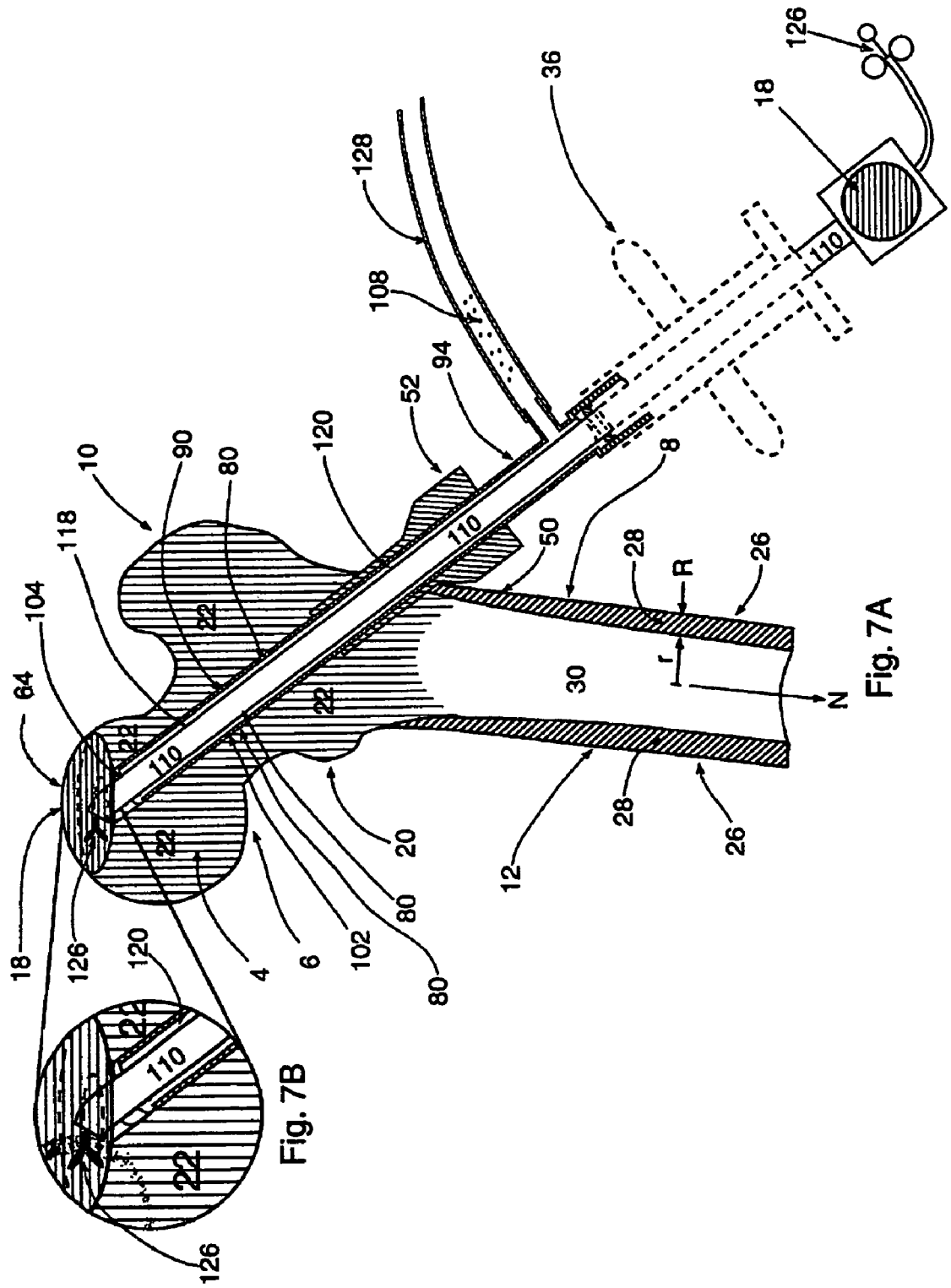

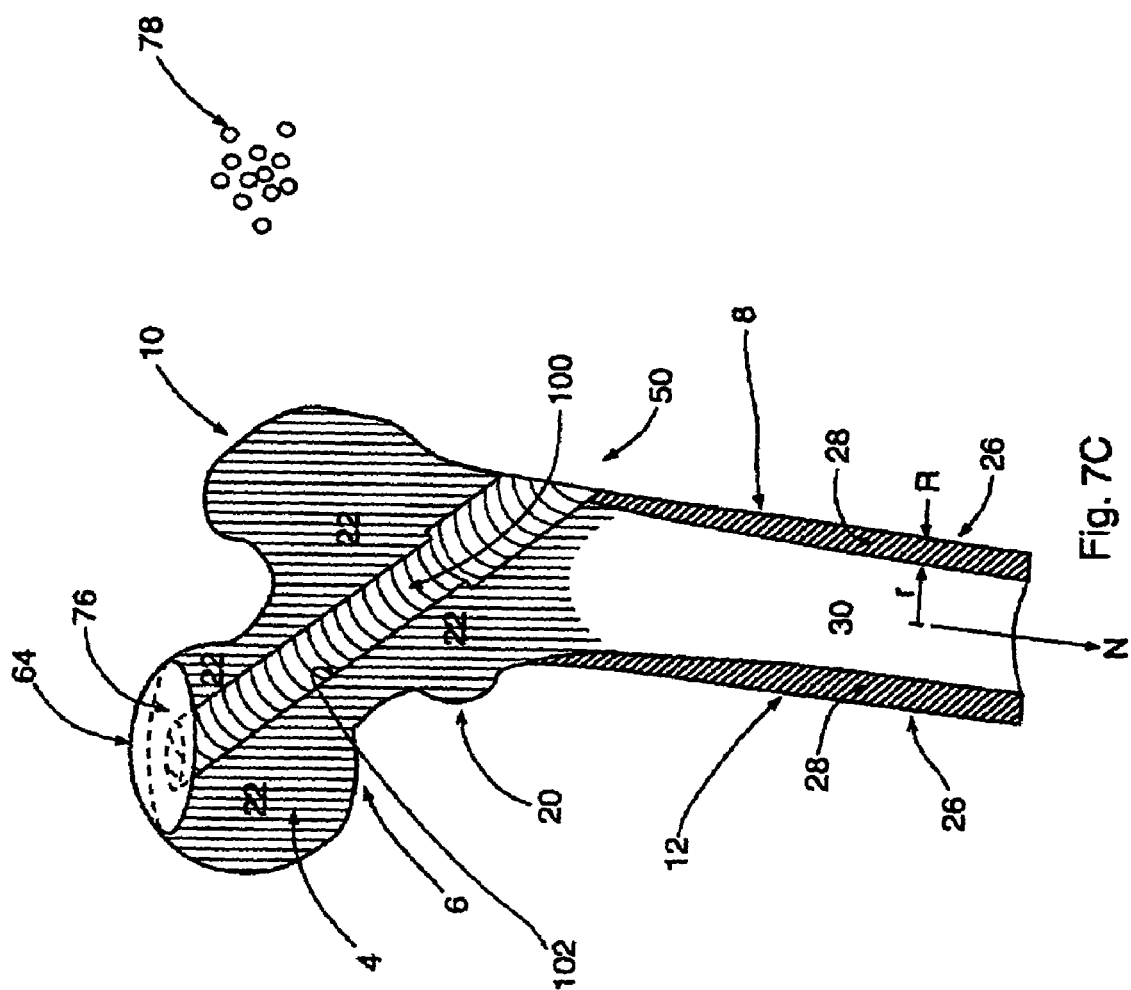

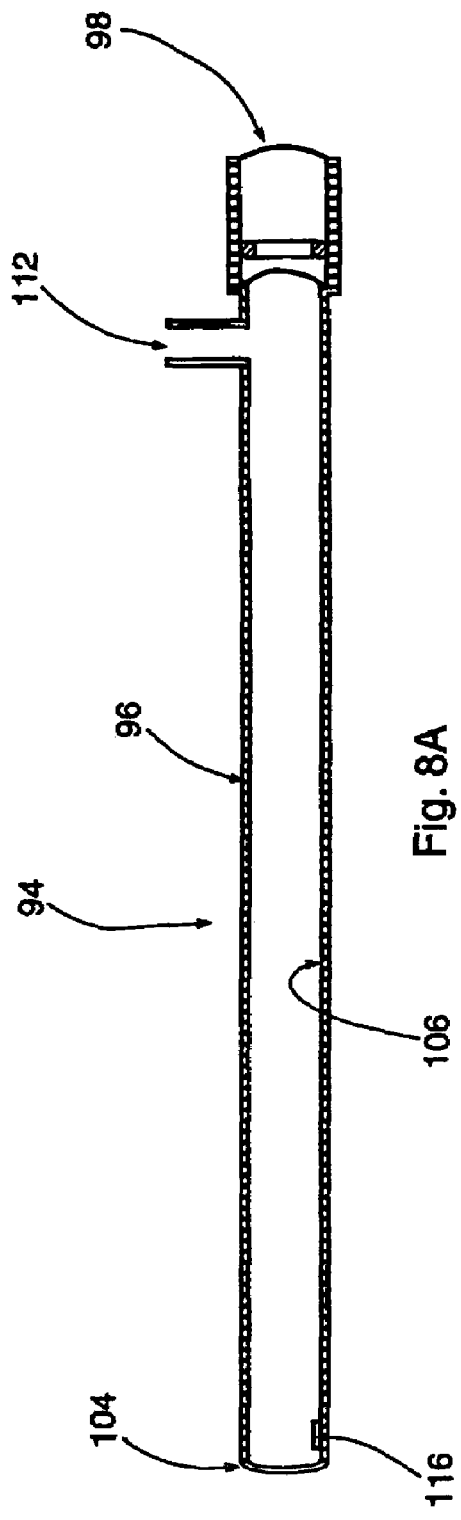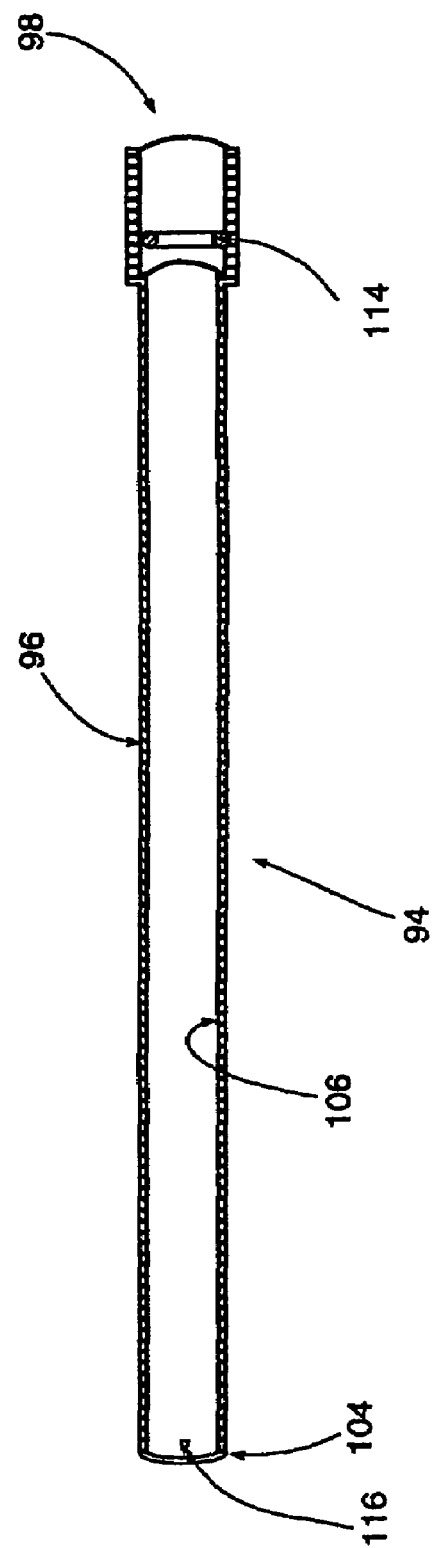

ENDOSCOPIC BONE DEBRIDEMENT

This application is a divisional of U.S. patent application Ser. No. 09/957,817, filed Sep. 19, 2001, now abandoned, the contents of which are hereby incorporated by reference.

BACKGROUND OF THE INVENTION

1. Field of the Invention

Osteonecrosis of the femoral head in the young patient is a musculoskeletal disorder with growing concerns, particularly as osteolysis from particulate polyethylene wear debris compromises the longevity of a total hip arthroplasty. Approximately 20,000 new cases are reported each year, with an estimated 450,000 patients, on average, with ongoing disease in the United States. Lavernia et al. further reported in the Journal of the American Academy of Orthopaedic Surgeons in 1999 that osteonecrosis usually occurs during the prime of one's working years.

Osteonecrosis of the femoral head can be separated into two clinical categories, the symptomatic hip and the asymptomatic hip. Almost uniformly, 85% of symptomatic hips progress to collapse, irrespective of the stage of disease at the time of the initial diagnosis. It is often the asymptomatic hip wherein controversy arises regarding treatment. Urbaniak found in his series of asymptomatic patients that at least ⅔ would progress to collapse. Importantly, one may define impending collapse of the femoral head as greater than 50% head involvement in two radiographic orthogonal views. Bradway and Morrey, in the J of Arthroplasty 1993, found that a collection of 15 "presymptomatic" hips all collapsed. Consequently, proponents of core decompression recommend early diagnosis and treatment of disease, with the understanding that such a treatment regimen may not halt progression.

Many theories have been proposed to explain the pathogenesis of osteonecrosis of the femoral head, as the name itself seems to describe the end condition, dead or nonviable osteocytes surrounded by a matrix of mineralized bone. More importantly, at least five categories have been identified as a potential mechanisms underlining the basis for disease: (1) Direct Cellular Mechanisms, cells die as a result of chemotherapy of thermal injury; (2) Extraosseous Arterial Mechanisms, ischemic necrosis of the femoral head following a substantially displaced fracture of the femoral neck; (3) Extraosseous Venous Mechanisms, an observation supported by the work of Ficat and Arlet in which these investigators observed venous hypertension in all clinical stages of osteonecrosis. Interestingly, The Johns Hopkins University observed compensatory mechanisms in the venous outflow of the femoral head when the venous system was obstructed using a dog model, raising questions about the role of venous congestion in the pathogenesis of disease; (4) Intraosseous Extravascular Mechanisms, this finding is thought to be consistent with bone marrow edema often observed on magnetic resonance imaging; and (5) Intraosseous Intravascular Mechanisms, occlusion of small vessels in patients with sickle-cell disease and dysbaric exposure wherein emboli of fat or nitrogen bubbles are thought to lead to osteonecrosis of the femoral head.

At least four Stages of osteonecrosis are described to allow one to institute and compare various treatment regimens. The most frequently used staging system is that of Ficat and Arlet as follows: Stage I, normal plain film radiographs; Stage II, Sclerotic or cystic lesions without subchondral fracture; Stage III, Subchondral fracture (crescent sign), with or without articular incongruity; and Stage IV, osteoarthrosis with osteophytes. Other staging systems include those of Marcus et al., University of Pennsylvania System of Staging, Association Research Circulation Osseous (ARCO), and the Japanese Investigation Committee on Osteonecrosis wherein the location of the lesion determines the stage of disease.

At the histologic level, necrosis of the femoral head can be described as dead or nonviable osteocytes surrounded by a mineralized matrix of bone. In a retrospective study by Marcus and Enneking, 13 core biopsies had been performed to treat eleven patients with asymptomatic or silent hips in Stage I or Stage II disease. All core biopsies in their series demonstrated normal articular cartilage, necrotic subchondral bone, and creeping substitution (osteoclastic bone resorption followed by the infiltration of marrow mesenchymal cells within a fibrovascular stroma). These observations and those of Phemister, Bonfiglio and others suggest that the success of core decompression in the treatment of osteonecrosis of the femoral head, Stage I or II, partly depends on the ability of autologous bone graft to incorporate the necrotic segment of bone within the femoral head. However, these authors did not attempt to characterize the requirements for host bone incorporation beyond an adequate blood supply.

The diagnosis of osteonecrosis can be easily made on plain film radiographs, assuming the disease is at least Ficat and Arlet Stage II, combined with a thorough history with an emphasis on predisposing risk factors, principally alcohol and steroid use, and a complete physical examination. Magnetic resonance imaging (MRI) may add additional information but is not routinely necessary. The MRI, however, is particularly useful in the asymptomatic hip, Ficat and Arlet Stage I.

Treatment options for osteonecrosis of the femoral head are categorized into one of two major groups, non-operative and operative. Nonoperatively, limited clinical success has been observed in the treatment of the symptomatic hip. Mont and Hungerford reviewed the nonoperative experience in the medical literature and found that only 22% of 819 hips in several pooled studies had a satisfactory result. These authors refer to the location of the osteonecrotic lesion, medial versus lateral, and suggest that medial lesions are more likely to have a satisfactory outcome. This observation is consistent with a mechanical component having a dominant role in the progression of disease, irrespective of etiology. Operative treatment can be characterized as core decompression of the femoral head with or without bone grafting followed by at least six weeks of non-weight bearing. Brown et al. at the University of Iowa used a three-dimensional finite-element model to elucidate the stress distribution over the diseased femoral head so as to characterize the optimal placement of a decompressing core with respect to location, depth, and diameter. More importantly, Brown et al. further showed that the optimum mechanical benefit of appropriately placed cortical bone grafts in a decompressed femoral head is realized when such grafts are situated in direct mechanical contact with the subchondral plate. These authors used the gait cycle to identify peak stress in the femoral head during normal walking and concluded that when fibula grafts are appropriately placed they potentially afford relief of stress to vulnerable necrotic cancellous bone in the subchondral and superocentral regions of the femoral head, implying that osseous incorporation of the cortical bone graft may be ideal but not completely necessary in the prevention of collapse. Although Brown et al. outlined the importance of strategic placement of a cortical fibula graft, it is important to recognize that these authors assumed that the necrotic cancellous bone is at risk for an intra-substance fracture, in the absence of treatment and that such intra-substance structural failure is principally responsible for the progression of disease, i.e., collapse of the femoral head. One must consider that as a segment of the femoral head becomes increasingly necrotic, its modulus of elasticity may vary substantially from that of the surrounding cancellous bone, and that progression of disease is perhaps also failure of this surrounding bone at the necrotic host bone interface; the area of creeping substitution in the work of Bonfiglio et al. Although not a part of the investigative objective, Brown et al. additionally did not demonstrate how cyclic loading of a cortical bone graft beneath the subchondral plate influences the healing behavior of the surrounding necrotic bone at the host necrotic bone interface. More specifically, is bony union achieved at the necrotic host bone interface now that the necrotic bone is unloaded? Is the fibula strut really a load-bearing cortical graft to the extent that the surrounding necrotic bone no longer sustains a substantial cyclic load during gait? Does the fibula strut simply allow the joint reactive force to bypass the segment of necrotic bone thereby substantially reducing its micromotion? Does micromotion of the necrotic segment of bone cause pain? Does the pain spectrum associated with osteonecrosis suggest a nonunion at the necrotic host bone interface, an intraosseous nonunion? These questions and others are prompted by the observation of good to excellent outcomes in patients with Ficat and Arlet Stage I or Stage II disease treated with core decompression with vascular and avascular cortical bone grafts, keeping aside the retrospective results of Kim et al. presented at the 1998 Annual Meeting comparing vascular to avascular fibula struts in treating osteonecrosis. More importantly, patients have been shown to benefit from core decompression alone implying that increased intraosseous pressure may play a dominant role in the early stages of disease, whereas in the later stages, the necrotic bone is less ductile and behaves in a more brittle fashion giving rise to subchondral collapse as evidence for a mechanical component playing a dominant role in the progression of disease. Recently, Mont et al. reported in the Journal of Bone and Joint Surgery good to excellent results in two groups of six dogs, twelve osteonecrotic hips, treated with trans-articular decompression of the femoral head and bone grafting, with and without osteogenic protein-1. Although the authors sought to elucidate the difference in healing time, i.e., the time to graft incorporation between the two groups, the critical observation is that all twelve hips were treated with avascular autograft. Therefore, Mont's work in view of Brown et al. causes one to consider the role a vascularized fibula graft in the treatment of osteonecrosis of the femoral head. Does revascularization really occur?

The work of Brown et al. suggests that core decompression is substantially core debridement of the femoral head. However, as one attempts to adequately debride the femoral head of osteonecrotic bone, the diameter of the core, by necessity, becomes increasingly large because one is not able to mechanically debride bone from the femoral head at a right angle to the decompressing core. Further, strategic placement of a cortical bone graft beneath the subchondral plate simply provides means for bypassing the at risk necrotic bone and transfers the load during gait to the fibula strut, which is often secured at the lateral cortex of the femur with a single Kirschner wire. The addition of a "blood supply," vascularized fibula graft, in part relies on the work of Bonfiglio et al. Interestingly, actually "necrotic" autogenous bone stimulates osteoclastic bone resorption. In a recent issue of the Journal of Bone and Joint Surgery, Enneking showed in a histopathologic study that massive preserved human allografts (avascular bone) are slowly incorporated into host bone through limited bridging external callus and internal repair, even when rigid fixation is used to stabilize these grafts. Enneking suggests that the limited incorporation of allograft at cortical-cortical junctions could be enhanced with more recently developed osteoinductive substances. Importantly, however, is that Enneking observed enhanced bridging callus formation at allograft host junctions that were augmented with autogenous bone, and not increased internal repair that characterizes graft incorporation. Therefore, one is inclined to conclude that the newer osteoinductive substances may simply enhance external bridging callus and not internal repair. More importantly, Enneking observed bone at the allograft host junctions that lacked remodeling along the lines of stress. The critical issues here is that resorption must be followed by the infiltration of mesenchymal cells within a fibrovascular stroma for true incorporation to be established. Viable autograft appears to retain its ability to stimulate ongoing osteoclastic resorption whereas allograft lacks this ability, as it is principally osteoconductive. A blood supply may be more important at cortical-cortical junctions. Cortical-cancellous junctions depend on the nature of the host cancellous bone. Cortical bone will not incorporate necrotic cancellous bone as cortical bone lacks sufficient metabolic activity. However, given that cancellous bone is 8 times as metabolically active as cortical bone, one can expect incorporation of viable cortical bone at a cortical-cancellous junction. Within the growth plate, necrotic calcified cartilage stimulates osteoclastic resorption followed by the laying down of osteoid by osteoblast. In primary bone healing, osteoclast bore into necrotic segments of bone, which are then followed by the laying down of osteoid by osteoblast. One might recognize that in these examples, necrotic and avascular autogenous bone stimulates the infiltration of osteoclast and mesenchymal cells, and that external bridging callus in the presence of internal repair represents union. Enneking's work suggest that external bridging callus along human allograft bone is a surface event driven by local mesenchymal cells in the surrounding tissue while internal repair is limited as the cytokines germane to new bone formation within the allograft bone are lost during the sterilization process.

Einhorn et al. have shown that despite the great ingrowth of capillaries into fracture callus, the cell proliferation is such that the cells exist in a state of hypoxia. This hypoxic state could be favorable for bone formation, as in-vitro bone growth optimally occurs in a low-oxygen environment. Therefore, avascular autogenous bone in and of itself is not "bad" bone. Necrotic bone (a necrotic segment in the femoral head) retains its osteoinductivity and osteoconductivity. Osteoinduction is an avascular physiologic event dependent on BMP's, whereas osteoconduction is an avascular physical event dependent on the structural integrity of the inorganic extracellular matrix of bone. Urist in the Journal of Science in 1965 showed that "avascular" demineralized bone implanted in extra-skeletal sites would induce bone formation. Enneking has shown recently in the Journal that new bone formation can occur with massive allografts (necrotic bone) but internal repair (a physiologic event) is limited. More specifically, Hedrocel, a proprietary metal, will support the infiltration of osteoblast, with, the assumption that once infiltration is complete, new bone formation will ensue and ongoing remodeling (appositional new bone formation) will be sustained. Importantly, human allograft bone lacks osteoinduction sufficient to promote internal repair characteristic of bony union, as allograft bone is "processed" bone and consequentially may lose its ability to induce new bone formation. Necrotic or avascular autogenous bone retains its ability to induce and to conduct new bone formation, having a major requirement of stability and a healthy host bed. In this regard, as an osteoclastic front advances into the graft, avascular or necrotic, the mesenchymal cells that follow must continually receive the appropriate signals from cytokines (a physiologic event), and the graft must be sufficiently stable. Thus, one might consider the necrotic segment of the femoral head as a form of an unstable autograft and that the pathogenesis of osteonecrosis can be considered a mechanically unstable intra-osseous nonunion during the later stages of disease. An intra-osseous nonunion is to be distinctly differentiated from an extra-osseous nonunion wherein fibrous tissue characterizes the ununited bone. Clearly then, if stability of the necrotic segment of autogenous bone can be achieved, either through unloading of the necrotic bone or providing means for stabilization so as to facilitate internal repair where osteoinduction remains, union can be expected. The prevention of collapse and the absence of progression will characterize the extent and quality of union, i.e., internal repair.

To date, treatment modalities for osteonecrosis focus on attempts to deliver oxygenated blood to the necrotic bone within the femoral head. In a 1998 January/February article in the Journal of the American Academy of Orthopaedic Surgeons, Urbaniak describes a patent vascular pedicle along a fibula strut within a femoral head 5 days post-operatively. The patency of a typical vascularized fibula graft is usually assumed given the resolution of pain and the lack of progression of disease in a treated patient several years after the index surgery. The formal surgical procedure of decompression of the femoral head with vascularized fibula grafting usually requires prolonged surgery and is a demanding procedure. Vail and Urbaniak reported on donor site morbidity in 247 consecutive grafts in 198 patients at five years follow up. The authors observed an abnormality in 24% of limbs, a sensory deficit in 11.8%, and 2.7% had motor weakness. Other complications reported by Urbaniak and Harvey in 822 vascularized fibula grafts procedures include superficial wound infections in two patients, and thromboembolic events in three patients.

Recently, Zimmer began an IDE study using a proprietary material, Hedrocel (trabecular metal, tantalum) as a mechanical device to fill a surgically created void in a femoral neck of a decompressed femoral head. The trabecular metal has a compressive and an elastic modulus similar to cancellous bone. The current IDE study is designed to evaluate the safety and efficacy of trabecular metal in the treatment of patients with early stage disease. The frictional properties of trabecular metal interfaced against cancellous bone are outlined as means for securing the implant within host bone. More importantly, the current investigation is of a nature thought to promote revascularization of the femoral head. Trabecular metal is osteoconductive and promotes bony ingrowth. In this regard, bony ingrowth is unidirectional growth, i.e., growth from the surrounding bone into the trabecular metal implant. As an aside, Zimmer promotes an acetabular component in which trabecular metal overlies the outer surface of the component. Bony ingrowth is promoted along the surface of the implant as means for establishing its stable fixation. In this setting, unidirectional growth is ideal, i.e., bony ingrowth into the implant. However, trabecular metal or any synthetic component juxtaposed necrotic bone will not promote new bone formation in a direction away from the implanted device and toward the necrotic bone. Further, such a large porous material will create a physiologic demand on bone formation in a direction away from the necrotic bone toward and into the implanted device, when in fact the purpose of treatment, particularly vascularized fibula grafts, is to direct bony ingrowth into the necrotic bone, i.e., bone growth in a direction away from the fibula strut and into the necrotic bone.

More specifically, an acetabular component with trabecular metal on its outer surface has clinical value, whereas a mechanically stable column of trabecular metal within the femoral neck of a patient with osteonecrosis has less than obvious clinical value, as the bony ingrowth in this setting is in a direction away from the necrotic bone, thereby almost ensuring that the necrotic bone will not undergo sufficient internal repair as characterized by Enneking. One might surmise that complete debridement of the femoral head of necrotic bone and subsequent stabilization with trabecular metal may very well serve the clinical objectives of operative treatment. However, it is more prudent to stabilize the femoral head with autogenous cancellous bone. More succinctly, why discard a column of cancellous bone antecedent to the segment of necrotic bone within the femoral head? The antecedent cancellous bone is viable and is useful clinically. Clearly then, successful incorporation of a necrotic segment of bone requires bi-directional bony ingrowth. Bi-directional bony ingrowth is only available with viable cancellous autograft.

With the understanding as outlined, one might be principally inclined to (1) adequately debride a femoral head of necrotic bone, (2) replace the necrotic bone with viable cancellous bone, and (3) provide means for structural support to a region of overlying cartilage. It is the purpose of the invention described herein to achieve these objectives using a novel device and a minimally invasive surgical technique, without the use of a fibula strut.

2. Information Disclosure Statement

Bone grafting is among one of the most frequently performed surgical procedures by surgeons challenged with reconstructing or replacing skeletal defects. Over the years, several techniques have been devised to obtain and implant autologous bone. Scientist and clinicians have sought and defined the essential elements of bone healing and have further desired to secure these elements when considering the benefits of various types of bone grafting techniques. Recently, scientific inquiry has been directed toward understanding the role of bone morphogenic protein (BMP) in the process of new bone formation. What we have learned is that a simple fracture incites a tremendous cascade of events that lead to new bone formation, and that reducing this cascade to a product that can be sold is a difficult task if not impossible. Nonetheless, complex fractures continue to occur which orthopedic surgeons manage daily. Therefore, if one is to appreciate the invention at hand the essentials of fracture healing and new bone formation must be understood.

The essential elements required for bone regeneration are osteoconduction, osteoinduction, and osteogenic cells. In this regard, autogenous bone is the gold standard for bone harvesting. Cancellous bone, as does cortical bone, contains all of these elements but lacks structural integrity. Cortical bone has structural integrity but is limited in quantity. At the histologic level, cortical bone is 4 times as dense as cancellous bone, and cancellous bone is 8 times as metabolically active as cortical bone. Further, clinicians have recognized the consequences of donor site morbidity and prolonged hospitalization after a traditional harvesting technique. To circumvent some of these issues, numerous synthetic bone like products have been made available for general use. Each product attempts to exploit one or more of the three essential elements of bone regeneration described above. Although many of these products, e.g., Pro Osteon, INTERPORE, Collagraft, ZIMMER and others are unique, they remain expensive.

To define a less invasive technique for bone harvesting, percutaneous methods have been described. The recently developed techniques simply involve using a coring cylindrical device to obtain a segment of bone. David Billmire, M.D.

describes this technique in his article, Use of the CORB Needle Biopsy for the Harvesting of Iliac Crest Bone Graft, PLASTIC AND RECONSTRUCTIVE SURGERY, February 1994. Billmire makes no effort to ensure the quality of the harvested bone but rather describes a power-driven counter-rotating hollow needle as cutting through bone and soft tissue. Michael Saleh describes a percutaneous technique for bone harvesting in his article, Bone Graft Harvesting: A percutaneous Technique, Journal of Bone and Joint Surgery [Br] 1991; 73-B: 867-8. The author describes using a trephine to twist and lever out a core of bone of 8 mm in size. INNOVASIVE DEVICES describes using their COR™. System for arthroscopic bone graft harvesting. This system describes a disposable cutter having a distal cutting tooth projected into the lumen of the Harvester. This cutting tooth ensures that all harvested osteochondral bone grafts will have a uniform dimension. This cutting tool also serves as means for removing the harvested bone from its donor site. Further, the plunger of the COR™. System is used to disengage gently the harvested bone so as to maintain the overall length of the graft. This concept is absolutely essential to the successful use of the COR™. System as these precisely obtained samples of osteochondral bone are implanted into pre-drilled osteochondral defects within the knee. Further, a vacuum of any sort could not be used on the COR™. System, as the vacuum would simply continue to extract water from the knee joint thereby failing to create an effective pressure drop across the harvested bone and loss of operative visualization. Brannon, in U.S. Pat. No. 6,007,496 describes the use of a vacuum apparatus to create a pressure drop across an osteopiston of bone. Scarborough et al., in U.S. Pat. No. 5,632,747 described a device for cutting short segment dowels from a bone mass.

When considering bone for grafting purposes, the recipient site must be considered as well. Failure to achieve bony union at a fracture site or bony fusion at a fusion site may be caused by several factors. Often, the blood flow is inadequate at the fracture site because of local trauma during the inciting event, as might be the case in osteonecrosis of the femoral head. Further, when considering augmentation of the healing process with bone graft, it is imperative that the grafted bone contains all of the essential elements germane to successful osseous regeneration, namely, osteoconductive elements, osteoinductive elements, and osteoprogenitor cells. Most current devices used for bone grafting focus on quantity, the osteoconductive portion of the harvested bone, and less so on quality, the osteoinductive portion of the harvested bone. Recently, bone substitutes have been developed and can be classified according to the following major categories: 1) Osteoconductive synthetics (Pro Osteon 500), 2) Osteoinductive allograft (Grafton), 3) Osteoinductive biosynthetics (OP-1), 4) Osteoinductive autologous bone marrow aspirates, 5) Osteoconductive/Osteoinductive combination synthetics, and 6) Gene therapy. When implanting the above bone graft substitutes, recognizing the usefulness of a collection of bone growth elements at the fracture site or those generated during the process of open reduction and internal fixation (ORIF) or any other bony procedure, such as posterior spinal instrumentation, has not been achieved through the development of a simple device to promote in situ bone grafting. In this regard, synthetic alternatives to bone grafting can be used as expanders that can be added to autogenous bone and mesenchymal cells harvested in situ at the fracture site or the surgical site. This approach will indeed ensure that all patients are given an optimal opportunity for bony union or bony fusion.

To recognize the issues at hand governing the invention described herein, a simple discussion of biomechanics, physiology, and general physics is warranted and presented in support hereof.

Bone is a viscoelastic material, and as such, it behaves predictably along its stress strain curve when axially loaded in either tension or compression. The key word here is viscoelastic. The prefix "visco" describes the fluid component of the material being tested and the suffix "elastic" describes the recoil potential of the material being tested. The ratio of stress:strain is Young's Modulus. Clearly, a spring is fully elastic. One may place a tension force on a spring, but when the tension is released, the spring recoils to its original length. A syringe, on the other hand, with a thin hypodermic needle attached, is considered viscoelastic. In other words, the amount of deformation observed is time dependent. Simply, the deformation will remain after the tension is removed. Consider one throwing Silly Putty against the ground and observing it bounce versus letting the material sit on a counter for several hours. One should appreciate that minimal deformation occurs when the Silly Putty bounces from the floor versus sitting it on a counter for several hours. The deformation is time dependent because of the internal fluid properties of the material; an amount of time is required to observe a net fluid flow. Bone behaves in a similar fashion, but has the additional property of being able to respond to a given stress by forming new bone. When bone fails to respond favorably, it fractures.

The physiologic properties of bone hinge on the fluid elements that govern bone regeneration, namely, bone morphogenic protein, various hormones, and osteoprogenitor cells. These fluid elements are important to the physiologic function of bone and are found within the bone marrow and the circulatory system. Appreciate that there is a net flow of these elements as bone bares a daily physiologic load during normal walking. Since the circulatory system is a closed system, a net loss of these fluid elements is not observed but rather continuous remodeling of bone and metabolic maintenance of the various cells and proteins as they age and become nonfunctional. Bone is incompressible above or below its elastic limit, i.e., Young's Modulus. Poisson's ratio is used to describe this behavior and is defined as follows:

$$v = -(\text{delta } d/do)/(\text{delta } 1/10) \tag{1}.$$

Poisson's ratio can be thought of as a measure of how much a material thins when it is stretched, consider taffy, or how much a material bulges when it is compressed. Regarding bone, one does not necessarily observe an increase in volume when it is compressed, but rather an increase in the density as bone remodels along the lines of stress, i.e., form follows function, Wolf's Law. When bone is compressed beyond its elastic limit, it fractures, i.e., it expands, therefore, its area will increase in a direction perpendicular to the line of force. The fracture observed occurs in the osteoconductive portion of bone, and a fluid flow will occur, as a result of the fracture, within the osteoinductive portion of bone.

The physiology of bone form and function is clear, but what a physician may observe through a series of x-rays may vary from patient to patient. Clearly then what we look for on a x-ray is evidence of healing, and in this regard, fracture healing is divided into at least four categories as follows: 1) inflammatory stage, 2) soft callus stage, 3) hard callus stage, and 4) remodeling stage. Each of these stages has clinical parameters that can be evaluated at the bedside. It is important to note, however, that any healing process in the human begins with clot formation; consider a simple laceration.

Thus, fracture healing begins with clot formation. However, this stage of fracture healing does not have a clinical parameter unless the fracture is considered an open fracture and the absence of bleeding is observed.

The continues fluid nature of whole blood (formed elements, i.e., blood cells; serine proteases, i.e., clotting factors; proteins, carbohydrates, electrolytes and hormones) while circulating in the vascular system is substantially maintained by the endothelial lining along the vessel walls. When these circulating serine proteases are exposed to subendothelial collagen or surfaces other than endothelial cells, i.e., abnormal surfaces, platelets aggregate and the clotting cascade is initiated. Blood without formed elements is considered plasma, while plasma without clotting factors is considered serum. A collection of autogenous bone growth elements is considered any and all factors germane to bone formation.

The clotting cascade is divided into two arms; the intrinsic pathway, i.e., local tissue trauma incites clot formation through exposure of the subendothelial collagen to circulating serine proteases and platelets; and the extrinsic pathway which incites clot formation through the activation of Factor VII serine protease and by tissue thromboplastin released from damaged cells. Both pathways then converge on Factor X serine protease. Regarding platelets, these cells are first to arrive and become adherent to injured tissue and form a platelet plug. Adherent platelets are activated platelets and as such release hemostatic agonist and autologous growth factors through a process of degranulation. The hemostatic agonists promote clot formation to ensure that the bleeding stops, while the autologous growth factors initiate the healing process of the injured tissue. Unique to bone is that its healing process is more regenerative of new bone formation as opposed to reparative which is more indicative of scar formation. Scar formation in fracture healing is a nonunion. Further, when bone fractures as a result of surgical or unintentional trauma, a collection of bone growth elements are generated directly within the fracture that contain both fluid and non-fluid components. Within the fluid component are platelets, blood and bone marrow mesenchymal cells, collagen and noncollagenous proteins, and small spicules of bone. The solid component is considered the bony fragments. ORIF is specifically designed to restore length and alignment of the fractured bone through rigid fixation of the non-fluid component. Bone grafting is used when it is determined preoperatively that the structural integrity and the quantity of the bony fragments are insufficient to allow ORIF. Clearly, the collection of bone growth elements required for bony union are present at the fracture site at the time of surgical (core decompression) or unintentional trauma. It stands to reason that in situ autologous bone growth elements, fluid and non-fluid, should be retained and used in conjunction with means for stabilizing the intra-osseous nonunion within the osteonecrotic femoral head. In situ autologous bone growth factors at a given fracture site unequivocally include the appropriate level of BMP's and other noncollagenous proteins at the various stages of fracture healing as described above. Understanding the physiology of new bone formation, a reparative process, will lend credence to how one should collect and use bone graft elements harvested in situ or from a second operative site. The invention described herein uniquely exploits the above principles so as to ensure the optimum chance for bony union.

SUMMARY AND OBJECTS OF THE PRESENT INVENTION

It is an object of the present invention to provide means to allow the endoscopic debridement of a segment of osteonecrotic bone within a femoral head.

It is yet a further object of the present invention to provide means to allow intra-osseous visualization of necrotic bone within the femoral head.

It is yet a further object of the present invention to ensure that the femoral neck remains substantially free of blood during endoscopic debridement of the femoral head.

It is yet a further object of the present invention to provide means for stabilizing the endoscope within the femoral head and neck so as to facilitate endoscopic debridement thereof.

It is yet a further object of the present invention to provide means to evacuate simultaneously small fragments of necrotic bone as they are debrided intra-osseously.

It is yet a further object of the present invention to provide means to tamponade an osseous blood flow within the femoral head and neck so as to enhance visualization of cancellous bone then visualized.

It is yet a further object of the present invention to promote all musculoskeletal surgeons to use autogenous bone in situ when bone grafting is required for new bone formation.

SUMMARY

The present invention describes a novel and unobvious method for debriding osteonecrotic bone from a femoral head intra-osseously under direct visualization. The osteoendoscopic cylinder of the present invention is directed into a surgically created osteocentral canal of a femoral neck so as to protect the surrounding cancellous bone of the femoral neck and to tamponade any bleeding therefrom. The distal portion of the osteoendoscopic cylinder is of a shape and a dimension so as not to compromise the integrity of an endoscope and render it nonfunctional. The distal end of the osteoendoscopic cylinder further includes means for orienting the surgeon within the femoral head as to where osteonecrotic bone may be debrided. The endoscope is slidably passed over a proximal securing member thereabout the proximal end of the osteoendoscopic cylinder and then further directed therein to allow direct visualization of osteonecrotic bone within the femoral head. The bone within the femoral head is irrigated via the endoscope thereby allowing one to determine visually the quality of the bone then visualized. A flexible probe, grasping instrument or reamer is passed into the femoral head via the endoscope and necrotic bone is debrided therefrom under direct visualization. The debrided fragments of bone are evacuated through a vacuum apparatus source situated proximally along the osteoendoscopic cylinder. After the femoral head is debrided of substantially all necrotic bone, the antecedent autogenous cancellous osteomedullary bone cylinder is returned orthotopically and compacted therein so as to bone graft in situ. The above procedure is accomplished using a minimally invasive surgical technique.

BRIEF DESCRIPTION OF THE DRAWINGS

FIG. 4A is the femoral head and neck as in FIG. 3A with a centralizing sleeve having been inserted into the lateral portal of entry. An osteomedullary cylinder is shown having been advanced proximally into the femoral head and neck axially, concentrically and centrally about the plunger pin so as to establish an autogenous cancellous osteomedullary bone cylinder having an osteoaxial canal.

FIG. 7A is a sectional view of the osteoendoscopic cylinder of the present invention wherein an endoscope is shown having been inserted therethrough and into the femoral head so as to facilitate debridement of the femoral head under direct visualization.

FIG. 7B is an enhanced sectional view of the femoral head wherein a grasper is shown extending from the endoscope and into the femoral head.

FIG. 8 is an enhanced view of the osteoendoscopic cylinder of the present invention wherein the orientation mark is shown in larger view.

DESCRIPTION OF THE PREFERRED EMBODIMENTS

Figure 1A:
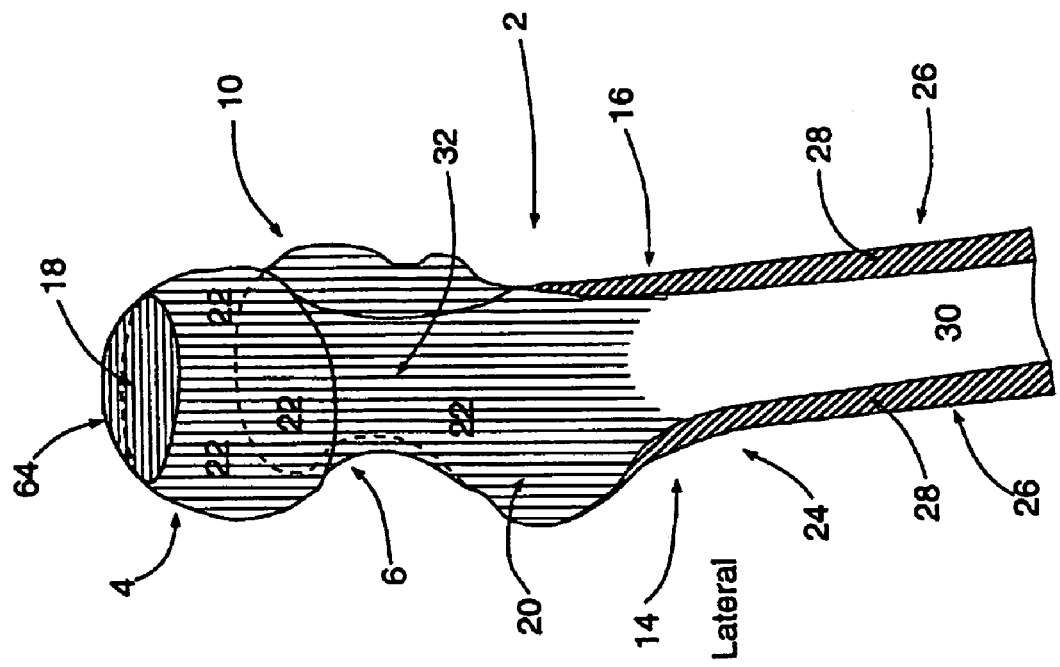
FIG. 1 is a sectional anteroposterior and lateral view of a femoral head and neck having an osteonecrotic segment bone within the femoral head.
Figure 1B:
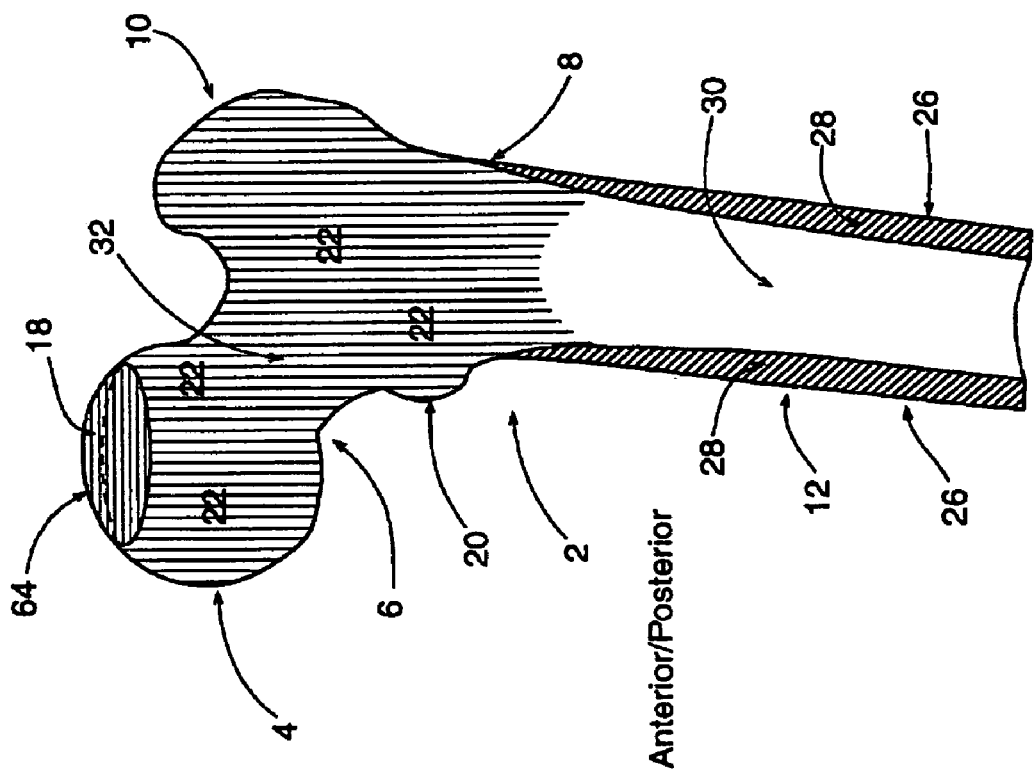

There shown generally at 2 in FIG. 1 is an anteroposterior view of a proximal femur having a femoral head 4 and a femoral neck 6 in anatomic confluency with a greater trochanter 10 and a lesser trochanter 20. Cancellous bone 22 is substantially confluent throughout the femoral head 4, the femoral neck 6 and the greater trochanter 10. In anatomic orientation described further herein, the femoral head 4 is situated proximally while the greater and lesser trochanters are situated distally. The femoral neck 6 establishes a cancellous bony pathway 32 therebetween the femoral head proximally and the greater and lesser trochanters distally. The greater trochanter 10 and the lesser trochanter 20 are in anatomic confluency with a femoral shaft 26 having an outer radius R. The femoral shaft 26 is comprised of cortical bone 28 circumferential to a medullary canal 30 having an inner radius r and a neutral axis N. In the anteroposterior view of the proximal femur, the femoral shaft 26 includes a medial cortex 12 and a lateral cortex 8. The medullary canal 30 establishes an areal moment of inertia I of the femoral shaft 26 to resist bending loads thereof to a substantial degree during normal gait. More specifically, the magnitude of compressive and tensile stresses during bending is defined as:

$$\sigma = My/I \tag{2},$$

where M is the bending moment and is defined as the perpendicular distance from a line of force to a point of interest, y is the linear distance from the neutral axis, and I is the areal moment of inertia. The areal moment of inertia I is defined as follows:

$$I = \tfrac{1}{4}\pi(R^4 - r^4), \tag{3}.$$

Equation 2 shows that the areal moment of inertia I is inversely proportional to the magnitude of compressive or tensile stresses within the femoral shaft 26.

The areal moment of inertia for a thin wall cylinder is given by:

$$I_t = \tfrac{1}{4}\pi r^3 t, \tag{4},$$

where t is the thickness of the cylindrical wall.

Referring now to a lateral view of the proximal femur in FIG. 1, the femoral head 4, the femoral neck 6, and the greater and lesser trochanters 10 and 20, respectively, are shown in anatomic confluency with the femoral shaft 26. In the lateral view of the proximal femur, the femoral shaft 26 having the medullary canal 30 includes a posterior cortex 14 and an anterior cortex 16. Now having described each of three orthogonal planes, a segment of osteonecrotic bone 18 is shown in both views of the proximal femur and is situated in the anterolateral portion of the femoral head 4.

Figure 2:
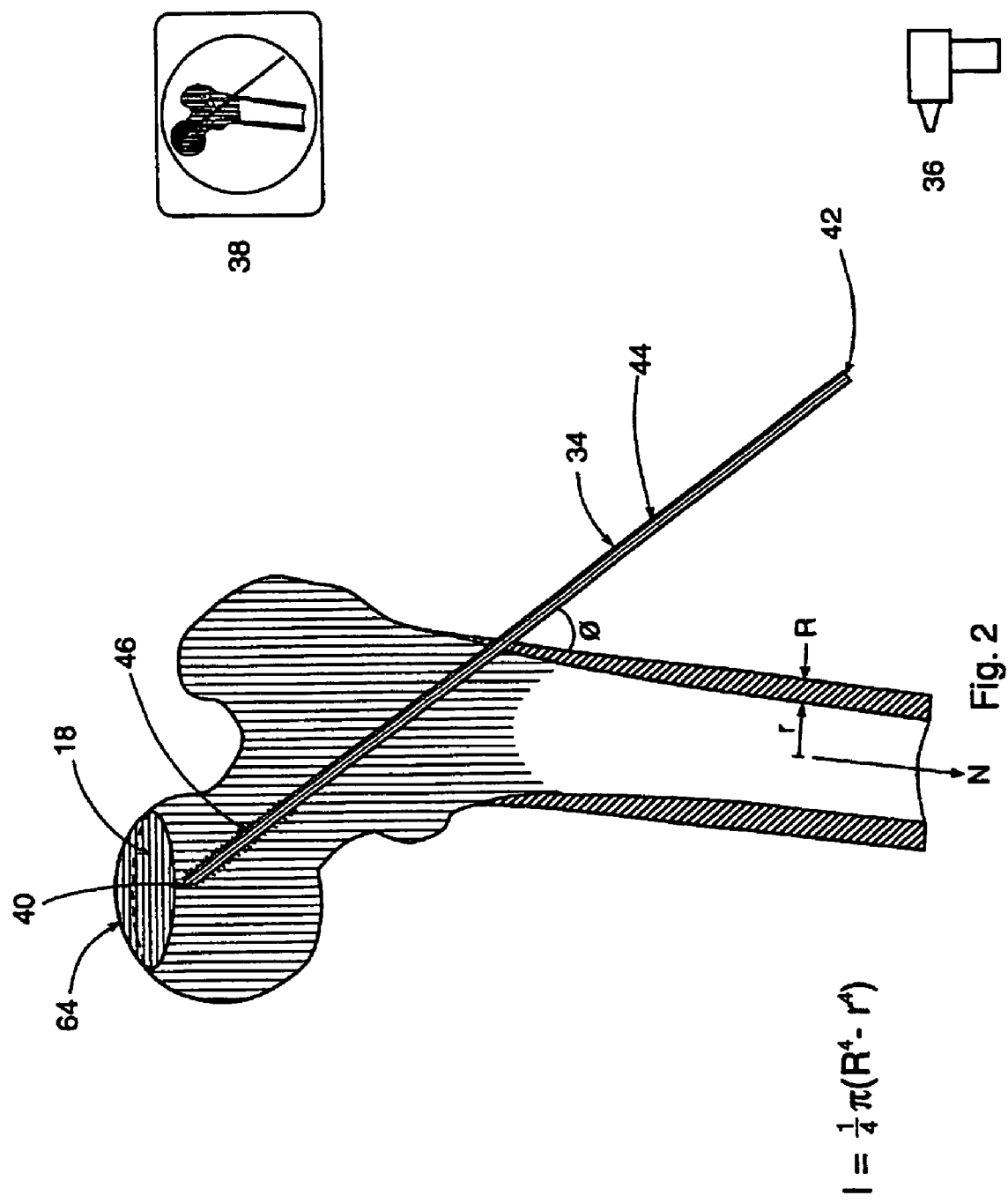
FIG. 2 is the femoral head and neck as in FIG. 1 with a plunger pin having been placed substantially centrally within the osteonecrotic segment of bone using fluoroscopic guidance.
Figure 3A:
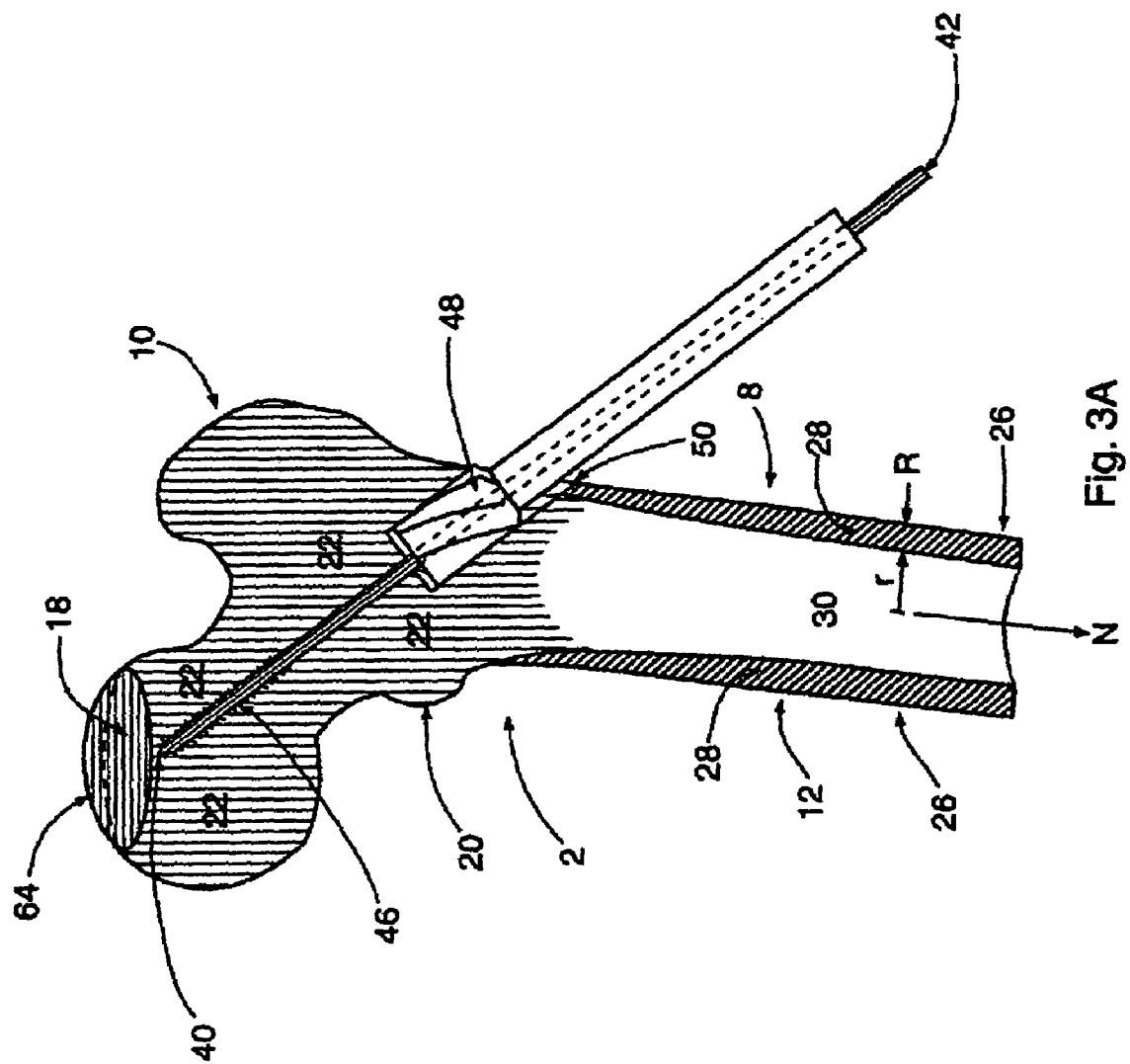
FIG. 3A is a sectional anteroposterior view of the femoral head and neck with a reamer establishing a lateral portal of entry along the lateral cortex of the femur whereas a cancellous bony remains undisturbed as shown in FIG. 3B.
Figure 3B:
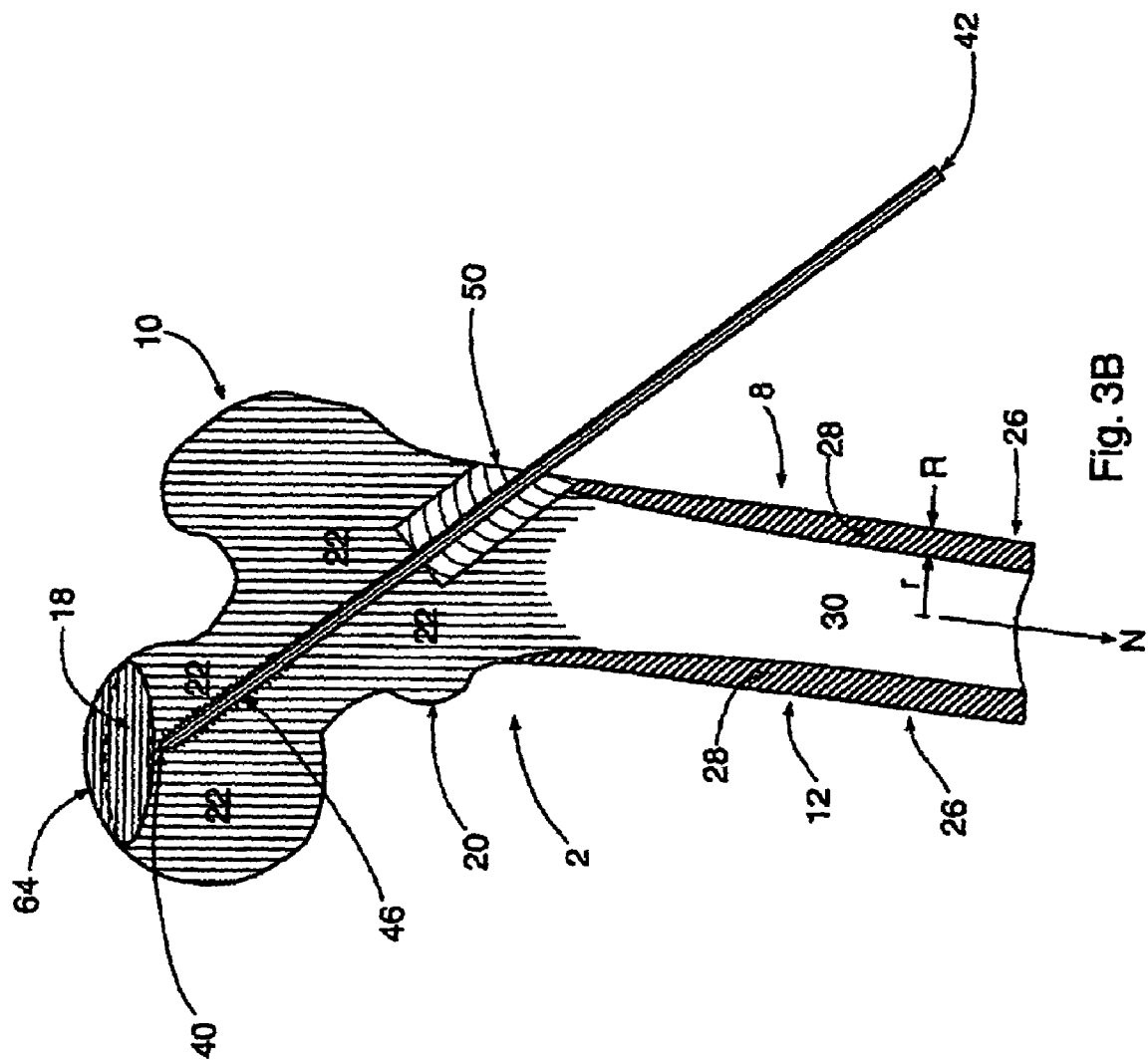

Turning now to FIG. 2, the proximal femur of FIG. 1 is shown in two orthogonal views, anteroposterior and lateral, having a plunger pin 34 of the present invention positioned substantially centrally within the segment of osteonecrotic bone 18. The plunger pin 34 is advanced proximally into the femoral head with use of a drill 36 and fluoroscopy 38 and first passes through the lateral cortex 8 and the cancellous bony pathway 32 of the femoral neck 6. The plunger pin 34 includes a sharpened distal end 40, a proximal end 42, and a longitudinal surface 44 having a friction capture region 46 distally situated thereabout the plunger pin. Descriptively, the distal end of the plunger pin is advanced into the femoral head 4. In FIG. 3A, a reamer 48 is passed over the plunger pin to establish a lateral portal of entry 50 leaving the cancellous bony pathway 32 undisturbed as shown in FIG. 3B.

Figure 4B:
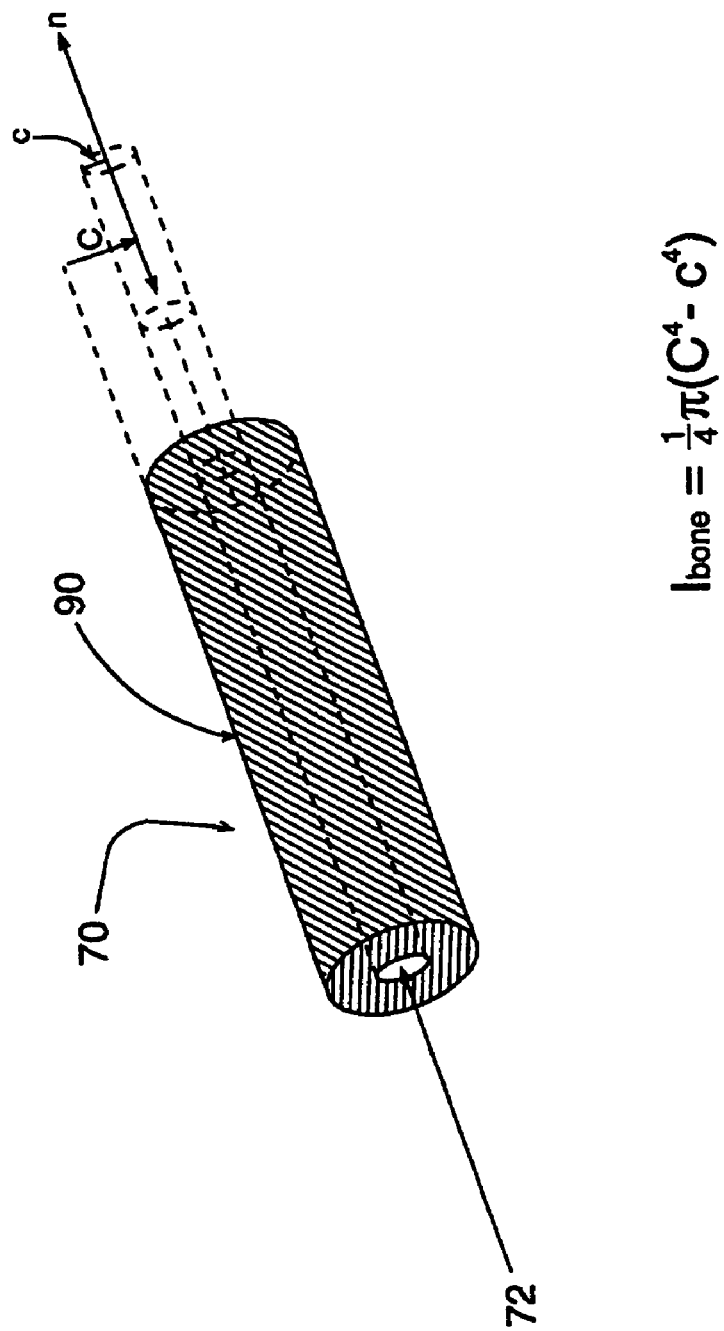
FIG. 4B is a geometric view of the autogenous cancellous osteomedullary bone cylinder having an osteoaxial canal.

Now turning to FIG. 4A, a centralizing sleeve 52 is shown within the lateral portal of entry 50 having the cancellous bony pathway 32 antecedent thereto the segment of osteonecrotic bone 18. An osteomedullary cylinder 74 of the present invention is passed through the centralizing sleeve and advanced proximally into the femoral neck 6 and femoral head 4 axially, concentrically, and centrally about the plunger pin 34. The osteomedullary cylinder remains physically separate from the plunger pin at all times. The osteomedullary cylinder 74 passes through the cancellous bony pathway 32 to a first position 54 juxtainferior to the segment of osteonecrotic bone 18. The osteomedullary cylinder 74 includes a distal bony end 56 and a proximal mechanical end 58 for mounting a handle 60 or the drill 36. The osteomedullary cylinder 74 further includes a first low friction inner surface 62 and a second low friction outer surface 66 in coaxial alignment so as to establish a material width 68 therebetween the inner and outer surfaces 62 and 66, respectively, of the osteomedullary cylinder. The material width 68 is of a dimension so as to establish a friction bony interface 80 therewithin the femoral neck 6. An autogenous cancellous osteomedullary bone cylinder 70 is uniformly porous having a length of at least 1 cm and an outer radius C and an osteoaxial canal 72 having an inner radius c from a neutral axis n is shown contained therewithin the osteomedullary cylinder 74. The plunger pin 34 is removed from the autogenous cancellous osteomedullary bone cylinder 70 by advancing the plunger pin proximally through the proximal mechanical end 58. In this regard, further shown proximally thereabout the proximal mechanical end 58 of the osteomedullary cylinder 74 is a proximal retaining support 92 of a size and shape adapted to prevent the removal of the autogenous cancellous osteomedullary bone cylinder 70 from the osteomedullary cylinder in a proximal direction. The proximal retaining support 92 being circumferentially situated thereabout the proximal mechanical end 58 is further of a size and dimension adapted to allow a displacement plunger 82 to pass therethrough in a distal direction and into the osteomedullary cylinder 74. More specifically, the autogenous cancellous osteomedullary bone cylinder 70 is only advanced into a proximal portion of the femoral head 4 and the femoral neck 6 by removal of the autogenous cancellous osteomedullary bone cylinder 70 from the osteomedullary cylinder 74 in a distal direction through the distal bony end 56. FIG. 4B shows the autogenous cancellous osteomedullary bone cylinder in greater visual detail so as to allow one to appreciate more completely the geometric properties thereof such that the autogenous cancellous osteomedullary bone cylinder is considered a hollow cylinder to be differentiated from a solid cylinder. Therefore, the areal moment of inertia $I_{bone}$ of the autogenous cancellous osteomedullary bone cylinder 70 is defined as:

$$I_{bone} = \frac{1}{4}\pi(C^4 - c^4), \quad (5),$$

wherein the geometric configuration thereof is of a construct to resist bending loads during normal gait as in Equation 2 above wherein the areal moment of inertia $I_{bone}$ is inversely proportional to the magnitude of compressive or tensile stresses. More importantly, Equation 2 does not reflect the material properties of bone as does Young's Modulus. Young's modulus of elasticity for cancellous bone may vary from approximately 10 MPa to 2,000 MPa, whereas that for cortical bone is approximately 17,000 MPa. In the geometric construct of the autogenous cancellous osteomedullary bone cylinder of the present invention, the osteoaxial canal 72 substantially functions to decompress the femoral head 4 of increased intraosseous hydrostatic pressure characteristic of osteonecrosis of the femoral head.

Figure 5:
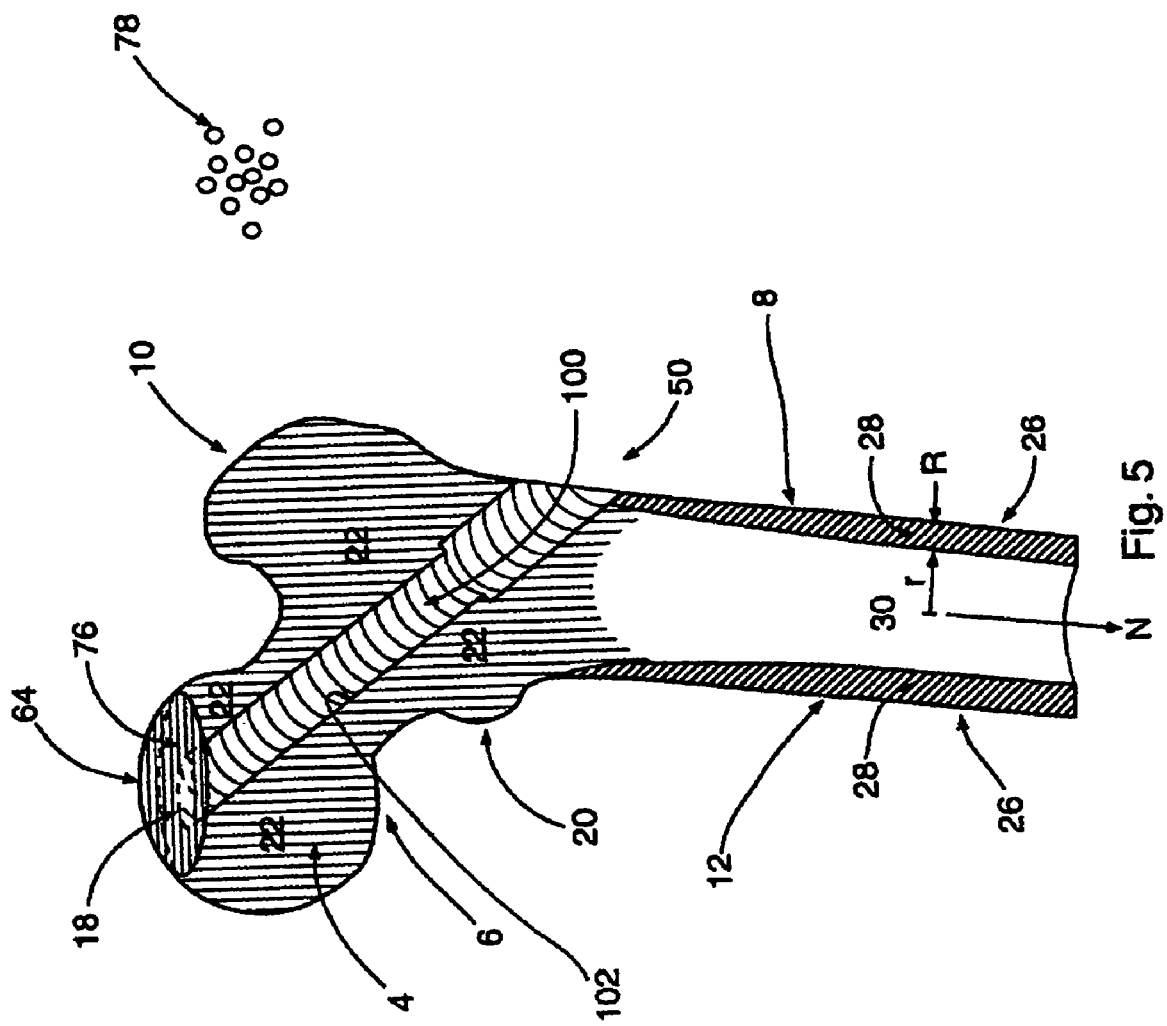
FIG. 5 is a sectional anteroposterior view of the femoral head and neck with the osteonecrotic segment of bone in structural confluency with an osteocentral canal.

FIG. 5 is a sectional view of the proximal femur having an osteocentral canal 100. The segment of osteonecrotic bone 18 is in structural confluency with the osteocentral canal having a longitudinal canal surface 102.

Figure 6:
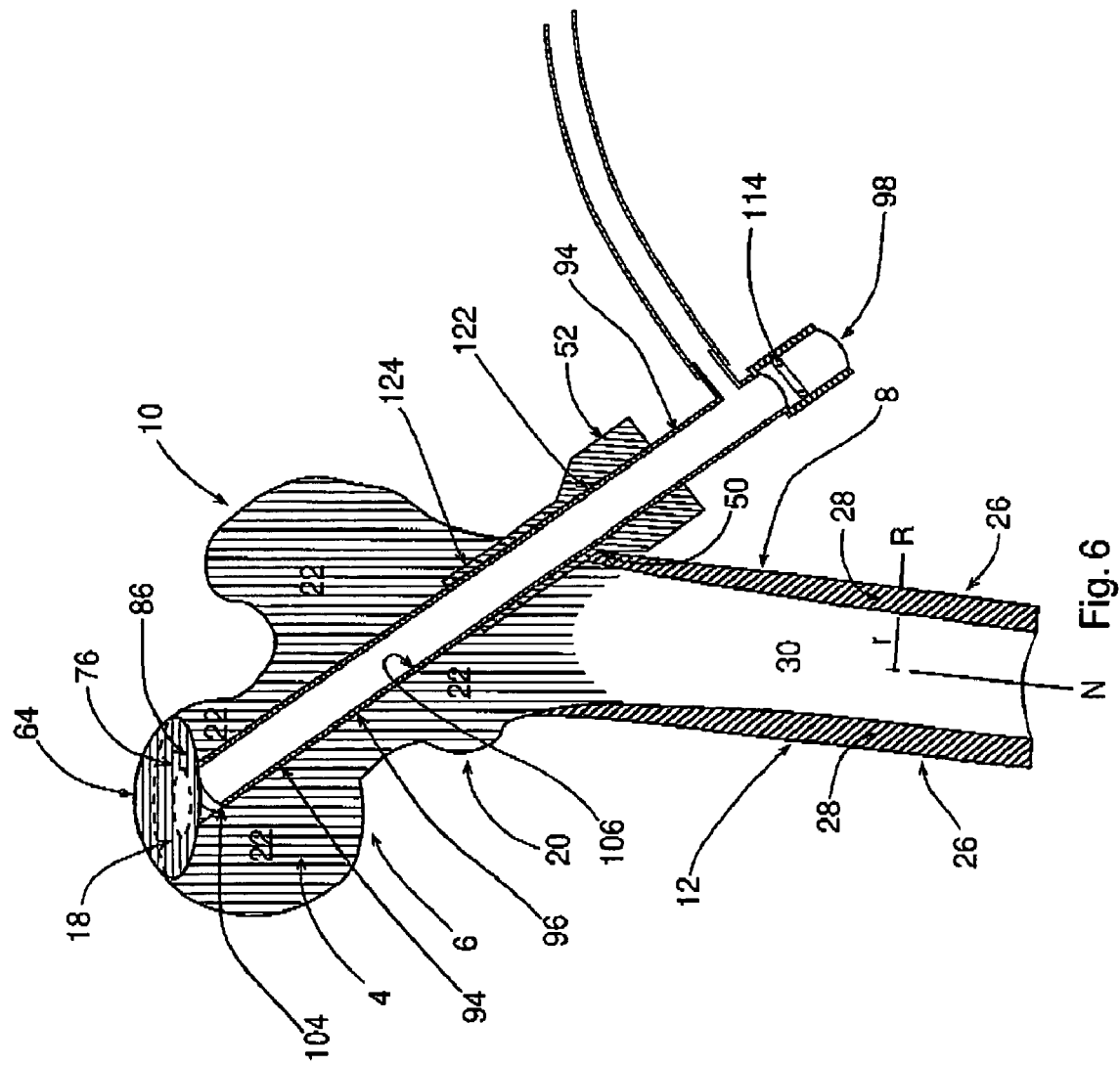
FIG. 6 is sectional view of the femoral head having the osteoendoscopic cylinder inserted therein. A vacuum apparatus source is shown for removing osteonecrotic bone fragments debrided from the femoral head.
Figure 9:
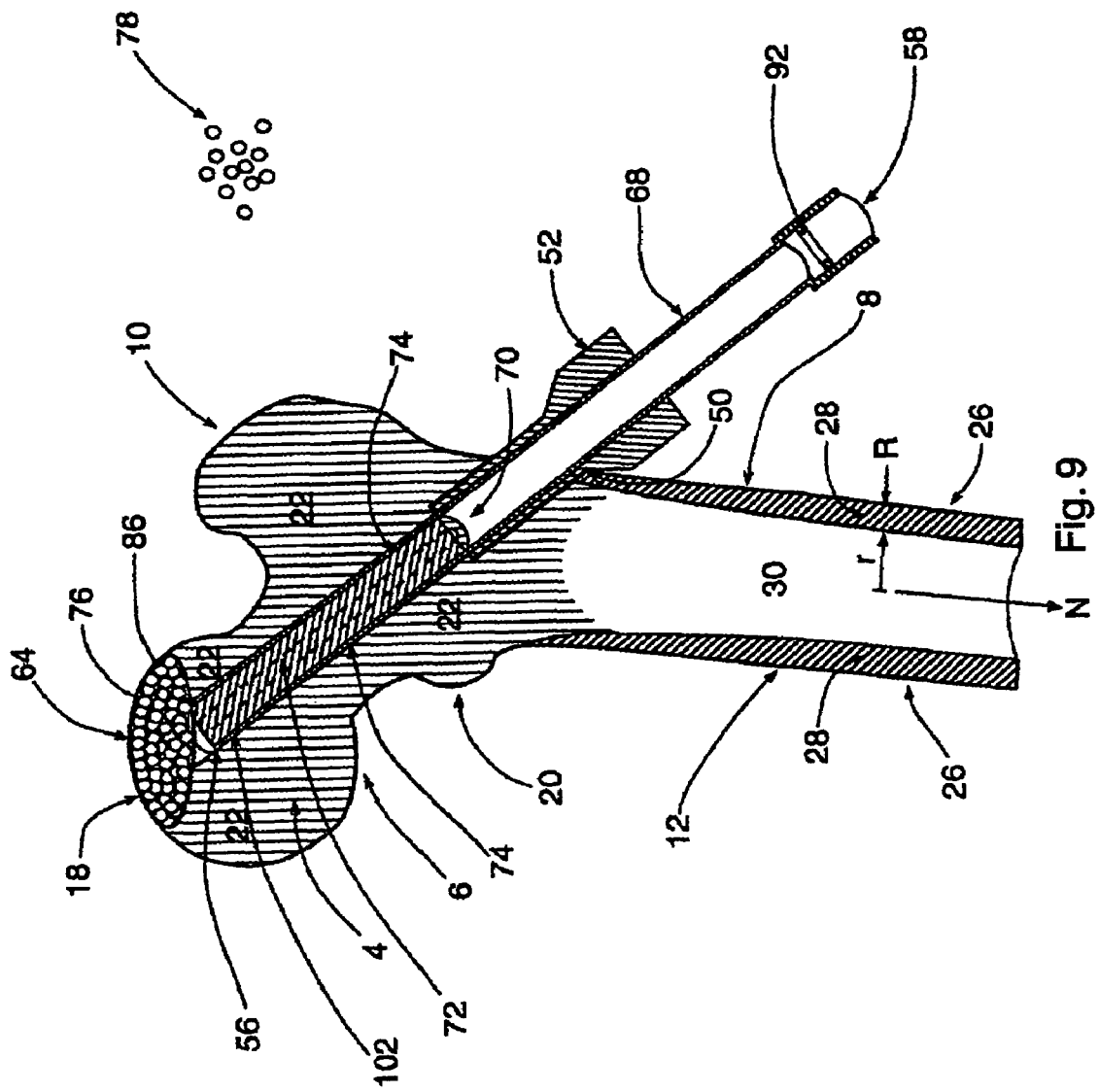
FIG. 9 is a sectional anteroposterior view of the proximal femur after having replaced the segment of osteonecrotic bone of FIG. 4A with bone graft. The autogenous cancellous osteomedullary bone cylinder is further shown having been advanced proximally to a second position juxtainferior to the bone graft. A friction bony interface is shown circumferential to the autogenous cancellous osteomedullary bone cylinder.
Figure 10A:
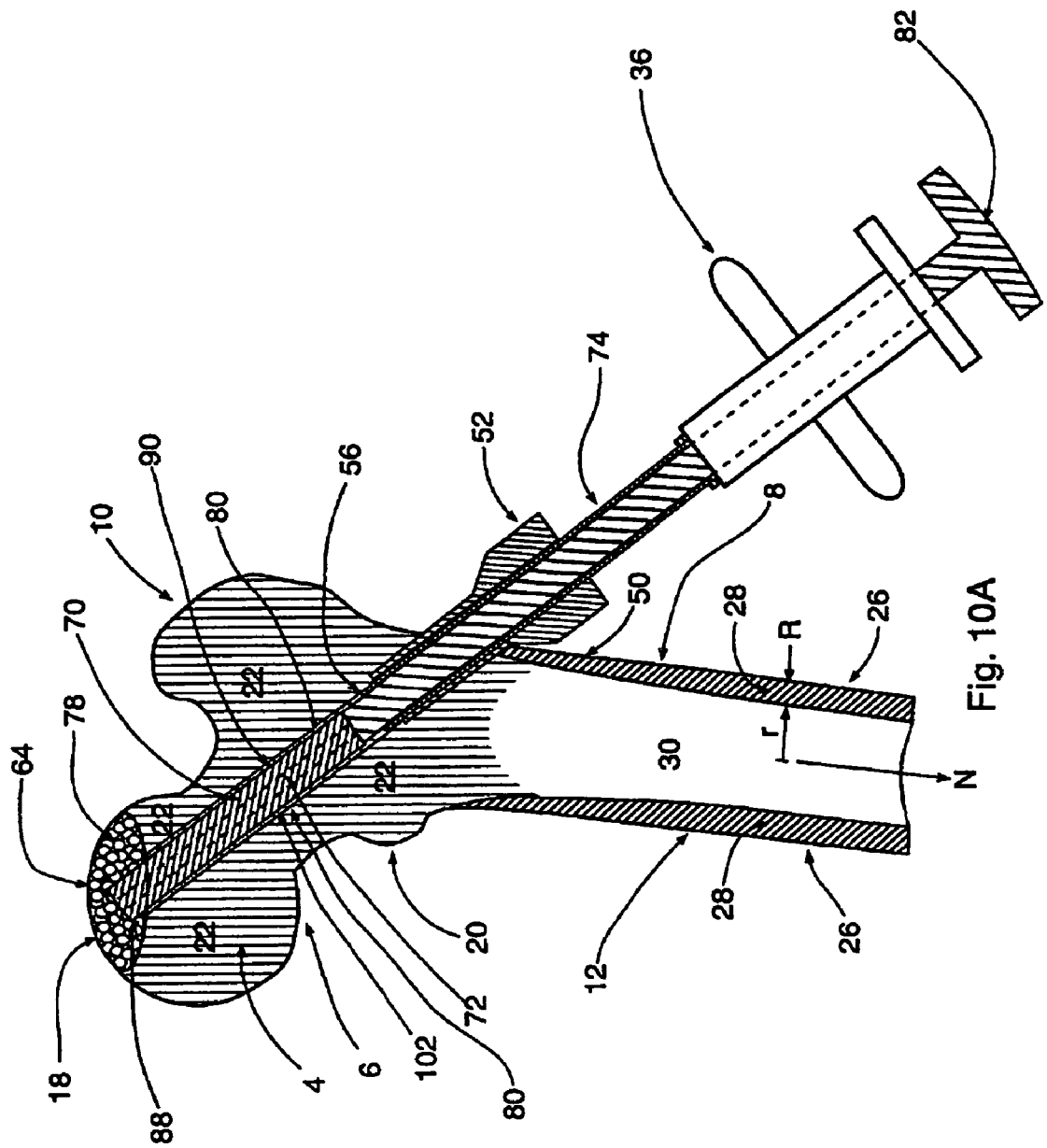
FIG. 10A is a sectional anteroposterior view of the proximal femur after having advanced further the osteomedullary bone cylinder to a third position juxtainferior to a region of overlying cartilage so as to provide mechanical support thereto within the osteocentral canal.
Figure 10B:
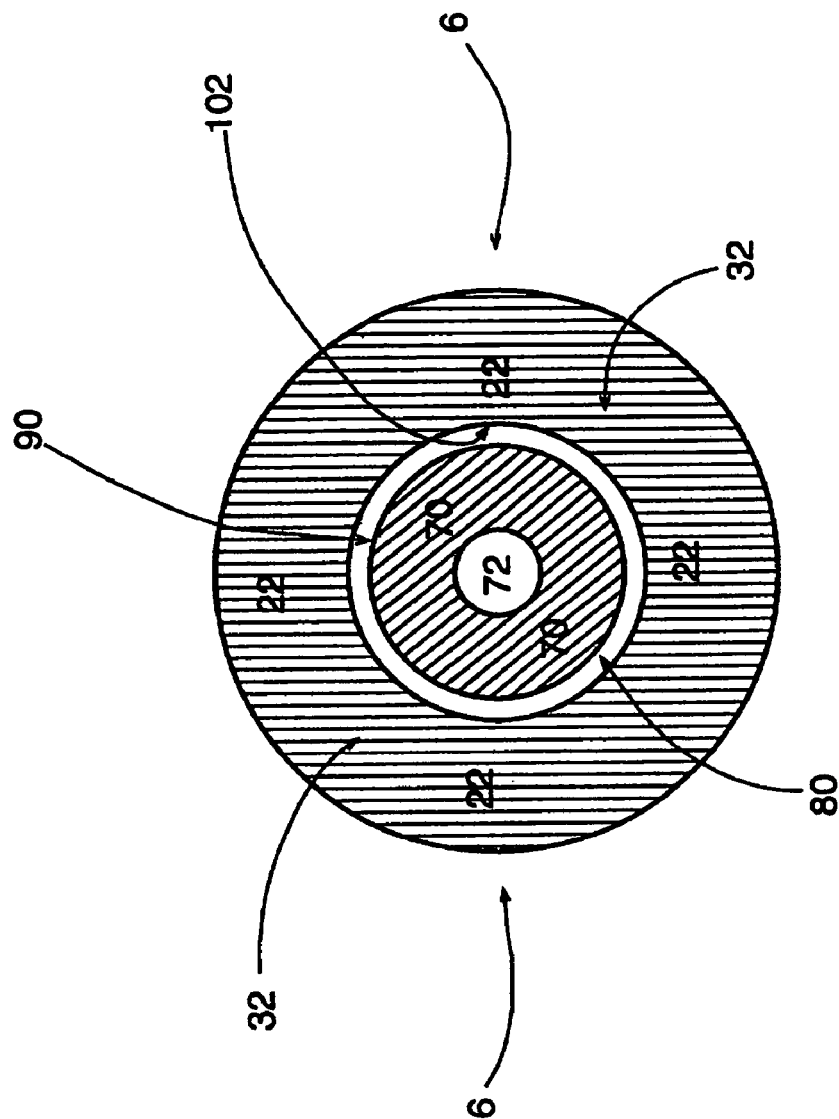
FIG. 10B is a sectional view of the proximal femur as in FIG. 7A having the centralizing sleeve, the plunger pin, and the osteomedullary cylinder removed therefrom.
Figure 10C:
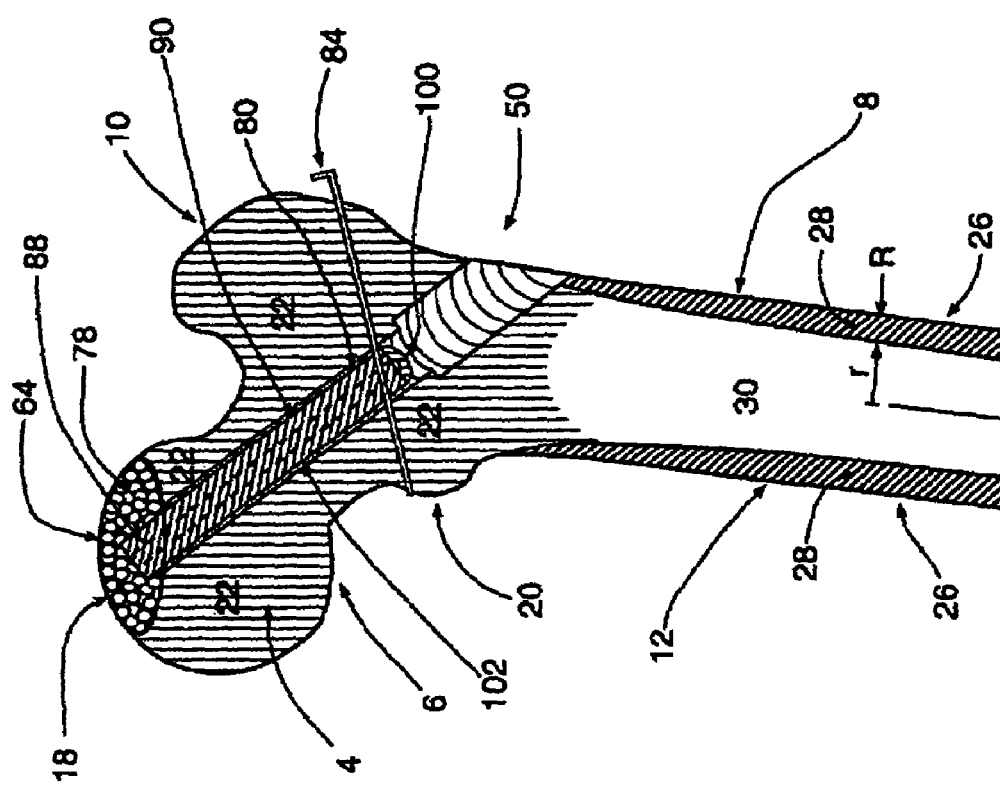
FIG. 10C is a sectional view of the proximal femur showing the completed procedure.

Turning now to FIG. 6 there shown is the osteoendoscopic cylinder 94 having been inserted into the osteocentral canal 100. The osteoendoscopic cylinder 94 includes an outer bony contact surface 96 of a dimension adapted to contact the longitudinal canal surface 102 so as to tamponade bleeding therefrom, and an inner visual surface 106. The outer bony contact surface 96 is further of a size and dimension adapted to establish a hermetic seal at the juncture thereof and the longitudinal canal surface. A hermetic seal is also be desirable at the juncture of the centralizing sleeve 52 and an inner bony surface 124 of the lateral portal of entry 50, and yet another hermetic seal at the juncture of the outer bony contact surface 96 and an inner centralizing surface 122 of the centralizing sleeve 52. The osteoendoscopic cylinder is of a size and dimension adapted to receive an endoscope coaxially along the inner visual surface and further includes a proximal handle end 98 and is shown having been engaged by the handle 60. A distal endoscopic end 104 is shown in proximity to the segment of osteonecrotic bone 18. Operationally situated thereabout the proximal handle end is a side opening 112 of a size and shape adapted to mount a vacuum apparatus 128 comprising of a transparent tube for evacuating a quantity of osteonecrotic bone fragments 108 debrided from the femoral head 4. The vacuum apparatus induces a low pressure environment within the femoral head so as to decompress an elevated intraosseous pressure therein. Further, the vacuum apparatus induces blood to flow from the cancellous bone then visualized within the femoral head with the endoscope thereby allowing the determination of the viability of the segment of osteonecrotic bone 18. Succinctly, does the cancellous bone within the femoral head bleed as evidence to support viability thereof? The side opening 112 is further of a size and dimension adapted to allow positioning thereof with respect to superior, inferior, anterior, or posterior anatomic quadrants of the proximal femur. FIG. 7A is a sectional view of the osteoendoscopic cylinder 94 within the femoral head wherein the distal endoscopic end 104 is situated juxtainferior to the segment of osteonecrotic bone 18. An endoscope 110 having a longitudinal material surface 118 is shown having been advanced into the osteoendoscopic cylinder substantially coaxially along the inner visual surface 106 so as to create a bony particle chamber 120 for collecting the quantity of osteonecrotic bone fragments 108 debrided from the femoral head. The endoscope passes into the osteoendoscopic cylinder after first passing through the handle 60 and over a proximal stabilizing support 114. The proximal stabilizing support is of a size and dimension adapted to allow distal and proximal advancement of the endoscope within the osteoendoscopic cylinder at all times thereby allowing visualization of the segment of osteonecrotic bone and the juncture thereof and surrounding cancellous bone. The proximal stabilizing support is further of a size and dimension adapted to prevent the flow of air at the juncture thereof and the longitudinal material surface 118 of the endoscope 110. Now with the endoscope within the osteoendoscopic cylinder 94, the surgeon may manipulate the optics thereof so as to visually observe the osteonecrotic bone and the cancellous bone within the femoral head. FIG. 7B is an enhanced sectional view of the proximal femur wherein a grasping instrument 126, a reamer, or a probe may be passed through the endoscope and into the femoral head as shown and in so doing, the femoral head may be debrided under direct visualization. Debridement of the femoral head creates an osteocavity 76 having a region of overlying cartilage 64 as is generally shown in FIG. 7C. The osteocavity 76 is in structural confluency with the osteocentral canal 100. Turning now to FIG. 8, situated thereabout the distal endoscopic end 104 and along the inner visual surface 106 is an orientation mark 116. The orientation mark 116 is of a size and shape adapted to ensure a first visualization thereof with the endoscope 110. The orientation mark is in orthogonal alignment with the side opening 112 so as to ensure operational and spatial orientation with respect to the superior, inferior, anterior and posterior bony quadrants within the femoral head at all times. More specifically, the surgeon may position the side opening 112 in a posterior direction and thereby position the orientation mark 116 anteriorly within the anterior bony quadrant of the femoral head. In this regard, debridement of the femoral head is strategic in that the quality and the location of the osteonecrotic bone then debrided under direct endoscopic visualization can be fully described. There shown in FIG. 9 is the osteocavity 76 of the femoral head 4 having been packed with a quantity of morselized cortical or cancellous bone graft 78. The packing of the femoral head 4, or replacement bone grafting as it may be called, is to a degree to completely fill the osteocavity 76 and to provide preliminary axial support to the region of overlying cartilage 64. FIG. 9 further shows the autogenous cancellous osteomedullary bone cylinder having been returned to a second position 86 juxtainferior to the now filled osteocavity 76. The osteoaxial canal 72 is in view. FIG. 10A shows the displacement plunger 82 having been passed through the osteomedullary cylinder 74 to further advance the autogenous cancellous osteomedullary bone cylinder distally into a proximal portion of the femoral head 4 to a third position 88 juxtainferior to the region of overlying cartilage 64 so as to provide mechanical support thereto. Importantly, the autogenous cancellous osteomedullary bone cylinder is of a length and dimension to provide mechanical support to the region of overlying cartilage and simultaneously remains in contact with the longitudinal canal surface 102 of the osteocentral canal 100. A stabilizing wire 84 is shown transfixing the autogenous cancellous osteomedullary bone cylinder so as to ensure the autogenous cancellous osteomedullary bone cylinder remains in the third position 88. A friction bony interface or a stable cylindrical fracture 80 is shown circumferentially situated to the autogenous cancellous osteomedullary bone cylinder 70 and is established therebetween a longitudinal bony friction surface 90 of the autogenous cancellous osteomedullary bone cylinder 70 and the longitudinal canal surface 102 of the osteocentral canal 100. FIG. 10B is a sagittal plane cross sectional view of the femoral neck 6 having the autogenous cancellous osteomedullary bone cylinder 70 centrally positioned therein. FIG. 10C shows the completed procedure wherein the osteomedullary cylinder 74, the displacement plunger 82, and the centralizing sleeve 52 have been removed.

What has been described is illustrative only and by no means is intended to represent all embodiments or modifications, as one might conceive an alternative embodiment, however, such alternative embodiment would not and could not deviate from the spirit of the invention. More importantly, the invention described herein avoids the need to create increasingly larger cores within the femoral neck in an effort to ensure adequate debridement of the femoral head. The invention described promotes immediate postoperative ambulation. Further, the invention described herein is simple and can be performed substantially percutaneously.

SPECIFICATION LISTING OSTEOENDOSCOPIC CYLINDER 2 proximal femur
4 a femoral head
6 a femoral neck
8 a lateral cortex
10 a greater trochanter
12 a medial cortex
14 a posterior cortex
16 an anterior cortex
18 a segment of osteonecrotic bone
20 a lesser trochanter
22 cancellous bone
24 a compaction sleeve
26 a femoral shaft
28 cortical bone
30 a medullary canal
32 a cancellous bony pathway
34 a plunger pin
36 a drill
38 fluoroscopy
40 a sharpened distal end
42 a proximal end
44 a longitudinal surface
46 a friction capture region
48 a reamer
50 a lateral portal of entry
52 a centralizing sleeve
54 a first position
56 a distal bony end
58 a proximal mechanical end
60 a handle
62 a first low friction inner surface
64 a region of overlying cartilage
66 a second low friction outer surface
68 a material width
70 an autogenous cancellous osteomedullary bone cylinder
72 an osteoaxial canal
74 an osteomedullary cylinder
76 a partially debrided osteocavity
78 morselized cortical or cancellous bone
80 a friction bony interface
82 a displacement plunger
84 a stabilizing wire
86 a second position
88 a third position
90 a longitudinal bony friction surface
92 a proximal retaining support
94 an osteoendoscopic cylinder
96 an outer bony contact surface
98 a proximal handle end
100 an osteocentral canal
102 a longitudinal canal surface
104 a distal endoscopic end
106 an inner visual surface
108 a quantity of osteonecrotic bone fragments
110 an endoscope
112 aside opening
114 a proximal stabilizing support
116 a plurality of orientation marks
118 a longitudinal material surface
120 a bony particle chamber
122 an inner centralizing surface
124 an inner bony surface
126
128
130

Thus having described the invention, what I desire to claim and secure by Letters Patent is:

1. A device for use in treating osteonecrosis, comprising:
an osteoendoscopic cylinder having a distal endoscopic end, a proximal handle end, an inner visual surface and an outer contact surface, wherein the distal endoscopic end includes an orientation mark along the inner visual surface and passing through a centralizing sleeve, said centralizing sleeve adapted to establish a hermetic seal at a juncture of the centralizing sleeve and a bony contact surface, said centralizing sleeve further comprising an inner surface wherein the outer contact surface of the osteoendoscopic cylinder and the inner surface of the centralizing sleeve are adapted to establish a hermetic seal at a juncture thereof, said osteoendoscopic cylinder further comprises an opening adapted to communicate with a vacuum apparatus wherein said orientation mark and said opening are aligned so as to provide spatial orientation of the bony contact surface.

2. The device of claim 1, further comprising an endoscope adapted to pass within said osteoendoscopic cylinder along said inner visual surface.

3. The device of claim 2, further including an instrument adapted to be passed through said endoscope and to debride necrotic bone.

4. The device of claim 3, wherein said instrument is selected from the group consisting of a grasping instrument, a reamer, and a probe.

5. The device of claim 1, further comprising a proximal stabilizing support adapted to prevent the flow of air at a juncture of said proximal stabilizing support and an endoscope and to allow said endoscope to pass distally and proximally within said osteoendoscopic cylinder along said inner visual surface.

6. The device of claim 1, further comprising a vacuum apparatus mounted on the opening in the osteoendoscopic cylinder.

* * * * *